United States Patent
Zhao et al.

(10) Patent No.: US 11,091,407 B2
(45) Date of Patent: Aug. 17, 2021

(54) PREHEATING PROCESS AND START-UP PROCESS FOR THE AMMOXIDATION REACTION

(71) Applicants: China Petroleum & Chemical Corporation, Beijing (CN); Shanghai Research Institute of Petrochemical Technology SINOPEC, Shanghai (CN)

(72) Inventors: Le Zhao, Shanghai (CN); Lianghua Wu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 0 days.

(21) Appl. No.: 16/629,747

(22) PCT Filed: Jul. 9, 2018

(86) PCT No.: PCT/CN2018/094945
§ 371 (c)(1),
(2) Date: Jan. 9, 2020

(87) PCT Pub. No.: WO2019/011199
PCT Pub. Date: Jan. 17, 2019

(65) Prior Publication Data
US 2020/0181039 A1  Jun. 11, 2020

(30) Foreign Application Priority Data

Jul. 10, 2017 (CN) .......................... 201710558010.0

(51) Int. Cl.
*C07B 43/08* (2006.01)
(52) U.S. Cl.
CPC ................................... *C07B 43/08* (2013.01)
(58) Field of Classification Search
CPC ...................................................... C07B 43/08
See application file for complete search history.

(56) References Cited

U.S. PATENT DOCUMENTS 3,766,092 A  10/1973 Aoki et al.
6,080,882 A  6/2000 Midorikawa et al.

FOREIGN PATENT DOCUMENTS

| CN | 104907013 A | 9/2015 |
| CN | 104907014 A | 9/2015 |
| CN | 206572483 U | 10/2017 |
| WO | 2015137925 A1 | 9/2015 |
| WO | 2015137926 A1 | 9/2015 |

*Primary Examiner* — Shawquia Jackson
(74) *Attorney, Agent, or Firm* — Novick, Kim & Lee, PLLC; Allen Xue

(57) ABSTRACT

The present invention relates to a preheating process and a start-up process for the ammoxidation reaction. The preheating process or the start-up process at least includes the step of heating the catalyst bed in the ammoxidation reactor while controlling the reactor operation linear speed to 0.03-0.15 m/s. The start-up process of the present invention has the advantages such as the significantly reduced launch time compared with the prior art and the operation safety.

51 Claims, No Drawings

PREHEATING PROCESS AND START-UP PROCESS FOR THE AMMOXIDATION REACTION

TECHNICAL FIELD

The present invention relates to a start-up process for the production of chemicals, and particularly to a start-up process involving an ammoxidation reaction. The present invention also relates to a preheating process for the ammoxidation reaction, which preheating process is particularly suitable as a preheating step of the start-up process.

BACKGROUND TECHNOLOGY

Acrylonitrile is an important chemical raw material, and is typically produced by the ammoxidation reaction of propylene (a representative substrate for the ammoxidation) in industry. Before the acrylonitrile production reaches a stable operation, it must pass through the start-up process. From the viewpoints of the production economy, the raw material consumption in the ammoxidation reaction and the like, it is desirable that the launch time taken by the start-up process is as short as possible.

Further, the feedstocks used for the ammoxidation reaction such as propylene and ammonia gas, and the reaction products such as acrylonitrile are all combustible materials, and there is a possibility of explosion in an oxygen-containing atmosphere. Therefore, during the entire operation of the acrylonitrile production, including during the start-up process, care must be taken to avoid explosion hazards to ensure the safety of the production and operation.

In addition to propylene, the same requirements exist for the ammoxidation reaction of other ammoxidation substrates such as butene and methanol.

SUMMARY OF THE INVENTION

The inventors of the present invention have diligently studied and found a novel preheating process and start-up process for the ammoxidation reaction, and thus have completed the present invention.

Specifically, the present invention involves the following aspects.

1. A preheating process for the ammoxidation reaction, which comprises a step of using a heating medium (preferably an oxygen-containing gas, especially air) to heat a catalyst bed in an ammoxidation reactor (preferably a fluidized bed reactor), wherein the reactor operation linear speed is 0.03-0.15 m/s (preferably 0.03-0.1 m/s), and/or, the input amount of the heating medium to the ammoxidation reactor is 54-276 $Nm^3/h/m^2$ (preferably 54-182 $Nm^3/h/m^2$).

2. The preheating process according to any of the previous aspects, wherein the catalyst bed is heated to a temperature of 360° C. or higher (preferably 370° C. or higher or 380° C. or higher, but preferably 500° C. or lower, 450° C. or lower, 400° C. or lower or 390° C. or lower).

3. A start-up process for the ammoxidation reaction, which comprises the following steps:

(1) heating a catalyst bed in an ammoxidation reactor (preferably a fluidized bed reactor) with an oxygen-containing gas (preferably air), wherein the reactor operation linear speed is 0.03-0.15 m/s (preferably 0.03-0.1 m/s), and/or, the input amount of the oxygen-containing gas to the ammoxidation reactor is 54-276 $Nm^3/h/m^2$ (preferably 54-182 $Nm^3/h/m^2$);

(2) continuously inputting ammonia gas to the ammoxidation reactor;

(3) continuously inputting an ammoxidation substrate to the ammoxidation reactor; and (4) optionally, adjusting the respective input amounts of the oxygen-containing gas, the ammonia gas and the ammoxidation substrate to the ammoxidation reactor to their respective predetermined values.

4. A start-up process for the ammoxidation reaction, which comprises the following steps:

(1) heating a catalyst bed in an ammoxidation reactor (preferably fluidized bed reactor) with an oxygen-containing gas (preferably air);

(2) continuously inputting ammonia gas to the ammoxidation reactor;

(3) continuously inputting an ammoxidation substrate to the ammoxidation reactor; and (4) adjusting the respective input amounts of the oxygen-containing gas, the ammonia gas and the ammoxidation substrate to the ammoxidation reactor to their respective predetermined values, wherein the reactor operation linear speed in the step (1), the reactor operation linear speed in the step (2), the reactor operation linear speed in the step (3) and the reactor operation linear speed in the step (4) respectively are 0.03-0.15 m/s, 0.04-0.18 m/s, 0.04-0.32 m/s and 0.5-1.2 m/s, preferably respectively are 0.03-0.1 m/s, 0.05-0.15 m/s, 0.05-0.20 m/s (or 0.04-0.17 m/s) and 0.65-0.95 m/s.

5. The start-up process according to any of the previous aspects, wherein in the step (1), the input amount of the oxygen-containing gas to the ammoxidation reactor is 54-276 $Nm^3/h/m^2$ (preferably 54-182 $Nm^3/h/m^2$).

6. The start-up process according to any of the previous aspects, wherein the ammoxidation substrate is selected from a group consisting of at least one of $C_{2-20}$ hydrocarbon (preferably $C_{2-10}$ hydrocarbon), $C_{1-10}$ monobasic alcohol or polybasic alcohol, one or more $C_{1-10}$ alkyl ethers of $C_{1-10}$ monobasic alcohol or polybasic alcohol, $C_{1-10}$ monobasic or polybasic carboxylic acid and one or more $C_{1-10}$ alkyl esters of $C_{1-10}$ monobasic or polybasic carboxylic acid, preferably at least one of $C_{2-10}$ linear or branched alkane, $C_{2-10}$ linear or branched olefin, $C_{6-10}$ aromatic hydrocarbon, $C_{1-10}$ monohydric alcohol, $C_{1-4}$ alkyl ether of $C_{1-10}$ monohydric alcohol, $C_{1-10}$ monocarboxylic acid and $C_{1-4}$ alkyl ester of $C_{1-10}$ monocarboxylic acid, more preferably at least one of $C_{2-4}$ linear or branched alkane, $C_{2-4}$ linear or branched olefin, $C_{1-4}$ linear or branched monohydric alcohol, $C_{1-4}$ linear or branched alkyl ether of $C_{1-4}$ linear or branched monohydric alcohol, $C_{1-4}$ linear or branched monocarboxylic acid and $C_{1-4}$ linear or branched alkyl ester of $C_{1-4}$ linear or branched monocarboxylic acid, particularly preferably at least one of propane, isobutane, propylene, isobutylene, methanol, ethanol, propanol, dimethyl ether, methyl ethyl ether, acetic acid and methyl acetate.

7. The start-up process according to any of the previous aspects, wherein in the step (1), the temperature of the catalyst bed is 360° C. or higher (preferably 370° C. or higher or 380° C. or higher, but preferably 500° C. or lower, 450° C. or lower, 400° C. or lower or 390° C. or lower), and/or, in the step (2), the temperature of the catalyst bed is 390° C. or higher (preferably 400° C. or higher, more preferably 400-440° C.), and/or, in the step (3), the temperature of the catalyst bed is 400-440° C. (preferably 400-430° C. or 410-430° C.), and/or, in the step (4), the temperature of the catalyst bed is 400-550° C. or 400-440° C. (preferably 400-440° C. or 425-440° C.).

8. The start-up process according to any of the previous aspects, wherein after the step (2) proceeds for 2-20 minutes (preferably 5-18 minutes), the step (3) begins, and/or, after the step (3) proceeds for 2-50 minutes (preferably 8-43 minutes), the step (4) begins, and/or, after the step (4) proceeds for 5-30 minutes (preferably 6-25 minutes), the start-up process ends, and/or, the time period from the beginning of the step (2) to the end of the start-up process is 10-100 minutes (preferably 20-60 minutes, more preferably 20-50 minutes).

9. The start-up process according to any of the previous aspects, wherein in the step (2), the target value of the input amount of the ammonia gas to the ammoxidation reactor is 7.5-110 $Nm^3/h/m^2$ (preferably 13.7-69.1 $Nm^3/h/m^2$ or 7.5-45.6 $Nm^3/h/m^2$), and the ratio of the target value of the input amount of the ammonia gas to the value of the input amount of the oxygen-containing gas is 1:2.5-7 (preferably 1:4-6.5 or 1:4-7), and/or, in the step (3), the target value of the input amount of the ammoxidation substrate to the ammoxidation reactor is 5.2-110.5 $Nm^3/h/m^2$ (preferably 9.13-65.8 $Nm^3/h/m^2$), and/or, in the step (4), the predetermined value of the input amount of the ammoxidation substrate is 110-160 $Nm^3/h/m^2$ (preferably 117-143 $Nm^3/h/m^2$), the predetermined value of the input amount of the ammonia gas is 120-23 $Nm^3/h/m^2$ (preferably 120-200 $Nm^3/h/m^2$ or 125-185 $Nm^3/h/m^2$), the predetermined value of the input amount of the oxygen-containing gas (preferably air) is 600-1600 $Nm^3/h/m^2$ (preferably 990-1600 $Nm^3/h/m^2$ or 1000-1500 $Nm^3/h/m^2$ or 1050-1400 $Nm^3/h/m^2$).

10. The start-up process according to any of the previous aspects, wherein the step (3) comprises the following steps:

(3-1) while maintaining the input amount of the ammonia gas to the ammoxidation reactor substantially constant, starting to input the ammoxidation substrate to the ammoxidation reactor; and (3-2) adjusting (preferably increasing) the respective input amounts of the oxygen-containing gas and the ammoxidation substrate to the ammoxidation reactor, wherein the reactor operation linear speed of the step (3-1) and the reactor operation linear speed of the step (3-2) are 0.04-0.18 m/s and 0.04-0.32 m/s respectively, preferably 0.05-0.15 m/s and 0.05-0.2 m/s respectively, or 0.05-0.15 m/s and 0.04-0.17 m/s respectively.

11. The start-up process according to any of the previous aspects, wherein the step (3-2) begins after the step (3-1) proceeds for 2-20 minutes (preferably 3-18 minutes), and/or, the next step (for example the step (4)) begins after the step (3-2) proceeds for 2-30 minutes (preferably 5-25 minutes), and/or, the time period from the beginning of the step (3-1) to the end of the step (3-2) is 2-50 min (preferably 8-43 minutes).

12. The start-up process according to any of the previous aspects, wherein in the step (3-1), the temperature of the catalyst bed is 400-440° C. (preferably 400-430° C. or 400-415° C.), and/or, in the step (3-2), the temperature of the catalyst bed is 400-550° C. or 420-450° C. (preferably 400-440° C. or 425-440° C.).

13. The start-up process according to any of the previous aspects, wherein in the step (3-1), the input amount of the ammoxidation substrate to the ammoxidation reactor is such an amount that the mole ratio of the ammoxidation substrate to the ammonia gas being input to the ammoxidation reactor reaches 1:4-7, preferably 1:4.5-6.5, and/or, in the step (3-2), the respective input amounts of the oxygen-containing gas and the ammoxidation substrate to the ammoxidation reactor are regulated (preferably increased), so that the mole ratio of the ammoxidation substrate to the ammonia gas being input to the ammoxidation reactor reaches 1:0.8-1:5 (preferably 1:0.85-1:4.5, or 1:1-1:1.5, or 1:1.05-1:1.3), and so that the mole ratio of the ammoxidation substrate to the oxygen-containing gas (preferably air, as the molecular oxygen) being input to the ammoxidation reactor reaches 1:4-1:30 (preferably 1:4.5-1:27, or 1:8.5-1:11.5, or 1:9-1:9.8).

14. The start-up process according to any of the previous aspects, wherein in the step (3-1), the target value of the input amount of the ammoxidation substrate to the ammoxidation reactor is 1.5-22.1 $Nm^3/h/m^2$ (preferably 2.74-13.8 $Nm^3/h/m^2$ or 1.5-11.4 $Nm^3/h/m^2$), and/or, in the step (3-2), the target value of the input amount of the ammoxidation substrate to the ammoxidation reactor is 5.2-110.5 $Nm^3/h/m^2$ (preferably 9.13-65.8 $Nm^3/h/m^2$), the target value of the input amount of the oxygen-containing gas to the ammoxidation reactor is 44.2-1270.7 $Nm^3/h/m^2$ (preferably 82.17-644.9 $Nm^3/h/m^2$).

15. The start-up process according to any of the previous aspects, wherein at the beginning of the step (3) or at the beginning of the step (3-1), the content of the molecular oxygen in the reaction tail gas (relative to the total volume of the reaction tail gas) is 7.5vol % or less, preferably 7-7.5vol %, and/or, at the beginning of the step (3-2), the content of the molecular oxygen in the reaction tail gas (relative to the total volume of the reaction tail gas) is 2vol % or less, preferably 0.5-2vol %.

Technical Effect

According to the present invention, one of the following technical effects can be implemented, or in a preferable situation, both of these technical effects can implemented at the same time.

(1) The launch time of the start-up process is significantly reduced, and correspondingly the consumption amounts of the ammoxidation reaction feedstocks (in particular the ammoxidation substrate and the ammonia gas) are significantly reduced. According to a preferable embodiment of the present invention, the launch time of the start-up process is generally 10-100 min, preferably 20-60 min, more preferably 20-50 min. According to another preferable embodiment of the present invention, the launch time of the start-up process is generally 80% or shorter, 70% or shorter, 60% or shorter, 50% or shorter, 40% or shorter, 30% or shorter, 20% or shorter, 10% or shorter, 5% or shorter, 1% or shorter, 0.5% or shorter, 0.25% or shorter, even 0.1% or shorter of the corresponding launch time of the prior art.

(2) The ammoxidation reaction is safe in operation and has a low explosion risk.

DETAILED DESCRIPTION OF THE INVENTION

The specific embodiments of the present invention are described in detail below, but it should be noted that the protection scope of the present invention is not limited by these specific embodiments, but is defined by the appended claims.

All publications, patent applications, patents and other references mentioned in this specification are incorporated herein by reference. Unless otherwise defined, all technical and scientific terms used in the specification have the meanings conventionally understood by those skilled in the art. In case of conflict, the definition in this specification shall prevail.

When a material, a substance, a method, a step, a plant, a component or the like is derived by an expression such as "well known to those skilled in the art", "prior art", "conventionally known in the art" or the like in the specification, the object derived by the expression encompass not only those conventionally used in the art at the time of filing this application, but also those that are not currently commonly used, but will become known in the art to be suitable for the similar purpose.

In the context of the present application, the term "ammoxidation reactor" must be understood according to the ordinary sense in the field of the production of chemicals (such as acrylonitrile and methacrylonitrile). For example, it refers to any reactor suitable for carrying out the ammoxidation reaction, including but not limited to fixed bed reactor and fluidized bed reactor, preferably fluidized bed reactor.

In the context of the present application, the term "start-up process" must be understood according to the ordinary sense in the field of the production of chemicals (such as acrylonitrile and methacrylonitrile). For example, it refers to the whole process beginning from preheating the catalyst bed in the ammoxidation reactor (corresponding to the preheating step) until the input amounts of all ammoxidation reaction feedstocks to said reactor reach the predetermined values at which the reactor is operated in a stable state. In particular, as the preheating step, it is sometimes referred to as a preheating process in the context of the present application. Further, in the context of the present application, the entire process from the end of the preheating step until the input amounts of all ammoxidation reaction feedstocks to the reactor reach the predetermined values at which the reactor is operated in a stable state is referred to as "launch process".

In the context of the invention of the present application, the term "launch time" refers to the overall time of the whole process from the end of the preheating step until the input amounts of all ammoxidation reaction feedstocks to the ammoxidation reactor reach the predetermined values at which the reactor is operated in a stable state, or refers to the overall time of the whole process from the beginning to the end of the launch process, usually in minutes or in hours.

In the context of the present application, the term "the reactor operation linear speed" or "the operation linear speed" or the like must be understood according to the ordinary sense in the field of the production of chemicals (such as acrylonitrile and methacrylonitrile). For example, it refers to the velocity of the fluid flowing in the reactor, and said linear velocity can be calculated according to the following formula (1):

$$V = \frac{(Q) \cdot (Tr) \cdot (Pn) \cdot N}{(S) \cdot (Tn) \cdot (Pr) \cdot 3600} \quad (1)$$

In the formula (1), Q is the sum of the flow rates of fluids into the reactor in the unit of $Nm^3/h$; S is the effective sectional area of the reactor in the unit of $m^2$; Tr is the temperature in the reactor in the unit of K; Tn is 273.15K; Pr is the top pressure of the reactor in the unit of Pa; Pn is the standard atmospheric pressure in the unit of Pa; N is the expansion ratio of the reaction gas; V is the reactor operation linear speed in the unit of m/s.

In the context of the present application, the term "input amount" refers to a flow rate of an ammoxidation reaction feedstock (for example the ammoxidation substrate, the ammonia gas and the oxygen-containing gas, in particular propylene, the ammonia gas and air) as being input to the ammoxidation reactor, i.e., an amount of the feedstock as being input, which amount can be calculated according to the following formula (2) in the unit of $Nm^3/h/m^2$, and means the volumetric flow of the gas under the normal condition per hour per square meter of the sectional area of the reactor.

$$q = \frac{(Q)}{(S)} \quad (2)$$

In the formula (2), Q is the flow rate into the reactor in the unit of $Nm^3/h$, and S is the effective sectional area of the reactor in the unit of $m^2$.

In the context of the present application, the term "target value" or "predetermined value" must be understood according to the ordinary sense in the field of the production of chemicals (such as acrylonitrile and methacrylonitrile). For example, it refers to a numerical number (also known as a final value) that a certain parameter (such as the input amount, the temperature, the pressure and the like) needs to reach at the end of the start-up process, the preheating process, the launch process or a certain operation step of these processes. At the beginning of said process or said operation step, said parameter can be any numerical number (known as the initial value), for example, zero or the final value. Specifically, for example, the parameter can reach the final value at the very start of the process or the operation step, and keep constant from start to finish or substantially keep that value (for example, the deviation is not beyond ±10%, preferably the deviation is not beyond ±5%). Alternatively, the parameter can change from the initial value to the final value. Regarding how the initial value changes to the final value, for example, as the process or the operation step proceeds, the parameter is changed from the initial value (by self-change or external intervention, preferably external intervention, for example, adjusting or controlling) to the final value. As the change, for example, an increase, a decrease or a combination thereof according to any change mode that is conventionally known in the art (such as a phasic mode, a linear mode, a jump mode, a pulse mode, a curve mode, a mode conforming to a certain formula or law, or the like) can be cited and is not particularly limited.

In the context of the present invention, the term "hydrocarbon" includes linear, branched or cyclic alkanes, linear, branched or cyclic alkenes, and aromatic hydrocarbons. One of these hydrocarbons can be used alone, or two or more of them can be used in combination.

In the context of the present application, the term "ammoxidation substrate" must be understood according to the ordinary sense in the field of the production of chemicals (such as acrylonitrile and methacrylonitrile). For example, it refers to any organic compound that can take part in the ammoxidation reaction with the ammonia gas and the molecular oxygen (for example to form the nitrile compound). As the organic compound, for example the following can be specifically exemplified: $C_{2-20}$ hydrocarbon (preferably $C_{2-10}$ hydrocarbon), $C_{1-10}$ monobasic alcohol or polybasic alcohol, one or more $C_{1-10}$ alkyl ethers of $C_{1-10}$ monobasic alcohol or polybasic alcohol, $C_{1-10}$ monobasic or polybasic carboxylic acid and one or more $C_{1-10}$ alkyl esters of $C_{1-10}$ monobasic or polybasic carboxylic acid. As the organic compound, for example the following can be further specifically exemplified: $C_{1-20}$ linear or branched alkane, $C_{2-10}$ linear or branched olefin, $C_{6-10}$ aromatic hydrocarbon, $C_{1-10}$ monohydric alcohol, $C_{1-4}$ alkyl ether of $C_{1-10}$ monohydric alcohol, $C_{1-10}$ monocarboxylic acid and $C_{1-4}$ alkyl ester of $C_{1-10}$ monocarboxylic acid. As the organic compound, for example the following can be further specifically exemplified: $C_{2-4}$ linear or branched alkane, $C_{2-4}$ linear or branched olefin, $C_{1-4}$ linear or branched monohydric alcohol, $C_{1-4}$ linear or branched alkyl ether of $C_{1-4}$ linear or branched monohydric alcohol, $C_{1-4}$ linear or branched monocarboxylic acid and $C_{1-4}$ linear or branched alkyl ester of $C_{1-4}$ linear or branched monocarboxylic acid. As the organic compound, for example the following can be particularly exemplified: propane, isobutane, propylene, isobutylene, methanol, ethanol, propanol, dimethyl ether, methyl ethyl ether, acetic acid and methyl acetate, propylene can be more particularly exemplified. One of these ammoxidation substrates or organic compounds can be used alone, or two or more of them can be used in combination. Furthermore, it can clearly be understood by those skilled in the art that, these ammoxidation substrates or organic compounds as one of the ammoxidation reaction feedstocks are generally present as a gas at least at the time when they enter the ammoxidation reactor, but can be present as a gas or a liquid or a combination before they come to the ammoxidation reactor; however there is no special limitation in this aspect in the present invention.

In the context of the present application, the term "ammonia gas" refers to the ammonia gas as one of the ammoxidation reaction feedstocks, which is present as a gas at least at the time when it enters the ammoxidation reactor, but can be present as a gas or a liquid or a combination before it comes to the ammoxidation reactor; however there is no special limitation in this aspect in the present invention. It is clear to those skilled in the art that, the ammonia gas may have any purity acceptable for said any ammoxidation reaction, or may also contain any impurity or diluent in any conventional manner known in the art (such as nitrogen or the like) that does not adversely affect said ammoxidation reaction; or may also be subjected to pretreatment (e.g., removal of harmful impurities, etc.) in any manner conventionally known in the art; however there is no special limitation in this aspect in the present invention.

In the context of the present invention, the term "oxygen-containing gas" refers to any gas containing the molecular oxygen. For example, the following can be specifically exemplified: air, oxygen, oxygen-enriched air, oxygen-depleted air, artificial air or a mixture of oxygen and other gas(es) (such as nitrogen or water vapor) and the like. It can be arbitrarily selected by those skilled in the art according to actual conditions or actual needs. However, air is particularly exemplified from the viewpoint of the operation ease and the production economy of the ammoxidation reaction.

In the context of the present invention, for the sake of simplicity of the description, any technical details or technical features not specifically illustrated, for example the information such as the operation mode of the fluidized bed, the mode of the ammoxidation reaction, the absorption method of the reaction tail gas, and the pretreatment method of the reaction feedstock, can be directly referred to the relevant information known in the art without substantial modifications, and thereby not described herein any more.

All percentages, parts, ratios and the like referred to in the present specification are by weight unless otherwise specified; or, if they do not meet the conventional knowledge of those skilled in the art on a weight basis, this conventional knowledge by those skilled in the art will prevail.

It is particularly noted that, two or more aspects (or embodiments) disclosed in the context of the present specification may be arbitrarily combined with each other, and the technical solutions thus formed (e.g. the method or the system) are a part of the original disclosure of the present specification.

According to the invention, a preheating process for an ammoxidation reaction is first mentioned. It is well known to those skilled in the art that, as the start-up process for the ammoxidation reaction, a step that a catalyst bed in an ammoxidation reactor is heated in some way (for example, by in contact with a heating medium) to a suitable temperature (referred to as preheating step), must be included. Here, the preheating process corresponds to the preheating step of the start-up process.

According to one aspect of the invention, the preheating process includes a step of heating a catalyst bed in an ammoxidation reactor with a heating medium. Here, as the heating medium, any heating medium which is known in the art to be used in the preheating step of the ammoxidation reaction can be used. As the heating medium, for example the following can be specifically exemplified: water vapor, nitrogen gas, and oxygen-containing gas, and air is particularly exemplified. One of these heating media can be used alone, or two or more of them can be used in combination.

According to one aspect of the present invention, in said preheating process, the reactor operation linear speed of the ammoxidation reactor is 0.03-0.15 m/s, preferably is controlled to be 0.03-0.1 m/s. To this end, the reactor operation linear speed can be conveniently achieved, for example, by adjusting the input flow rate or the input amount or the like of the heating medium to the ammoxidation reactor. The inventors of the present invention have surprisingly found that by limiting the reactor operation linear speed to the specific range, the launch time of the start-up process of the present invention can be significantly shortened, and the consumption amount of the ammoxidation reaction feedstock is also significantly reduced.

According to one aspect of the present invention, in said preheating process, the input amount of the heating medium to the ammoxidation reactor is generally 54-276 $Nm^3/h/m^2$, preferably 54-182 $Nm^3/h/m^2$. To this end, the input amount can be conveniently adjusted, for example, by adjusting the input flow rate of the heating medium to the ammoxidation reactor. The inventors of the present invention have surprisingly found that by limiting the input amount to the specific range, the launch time of the start-up process of the present invention can be significantly shortened, and the consumption amount of the ammoxidation reaction feedstock is also significantly reduced.

Without being bound by any theory, the inventors of the present invention believe that, by using a lower reactor operation linear speed or a lower input amount of the heating medium than those of the prior art, at the end of the preheating step, the total residual amount of the heating medium in the ammoxidation reactor is significantly reduced, whereby the total amount of the heating medium that needs to be treated (such as purged or consumed) in the subsequent launch process is also significantly reduced. For this reason, each of the ammoxidation reaction feedstocks can quickly reach the requirement stipulated by the stable operation of the ammoxidation reactor, resulting in that the consumption amounts of these reaction feedstocks are correspondingly significantly reduced. Moreover, particularly in the case where the heating medium is an oxygen-containing gas (particularly air), if the operation linear speed or the input amount exceeds the range specified by the present invention, since the amount of oxygen-containing gas entering the reactor is relatively high, a possibility that an incompletely reacted ammonia gas present in the subsequent launch process is instantaneously exposed to a certain concentration of oxygen is not excluded, which may lead to an explosion risk. In addition, if the operation linear speed or the input amount is lower than the range specified by the present invention, the fluidization quality of the catalyst is likely to be poor, so that the reaction process of the ammoxidation reaction feedstocks is insufficient, resulting in that the ratio of the unreacted ammonia gas in the system increases, thereby increasing the risk of explosion accident.

According to one aspect of the present invention, the catalyst bed in the ammoxidation reactor is heated through the preheating step or the preheating process to any temperature which can be expected when the ammoxidation reactor is preheated according to the prior art; for example the following can be specifically exemplified: 360° C. or higher, 370° C. or higher, or 380° C. or higher, or generally 500° C. or lower, 450° C. or lower, 400° C. or lower, or 390° C. or lower; however there is no special limitation in this aspect in the present invention. In addition, the time required or experienced by the preheating step or the preheating process is not limited by the present invention, and said time depends on whether or not each unit of the production plant has possessed the requisite condition of the start-up operation and in general it is also difficult to be pre-estimated. Moreover, as the temperature rise rate of the heating, any numerical value conventionally known in the art can be referred to, but as an example, it is usually 10-100° C./h.

According to one aspect of the present invention, in the preheating step or the preheating process, the pressure (gauge pressure) in the ammoxidation reactor is generally 0.030-0.060 MPa, preferably 0.030-0.055 MPa, but sometimes not limited thereto.

According to one aspect of the present invention, the catalyst to be used is not particularly limited, as long as it is any catalyst known in the art to render the ammoxidation substrate, the ammonia gas and the molecular oxygen to carry out the ammoxidation reaction (for example, to form a nitrile compound). As the catalyst, for example, the following can be exemplified: Mo—Bi based/support catalyst, Mo—Fe based/support catalyst, Mo—V based/support catalyst and the like that contain the active element Mo, or Sb—Fe based/support catalyst and the like that contain the active element Sb. One of these catalysts can be used alone, or two or more of them can be used in combination. Herein, as the support, the following can be exemplified: alumina and silica. One of these supports can be used alone, or two or more of them can be used in combination. As the particle size distribution, for example, the following can be exemplified: an average particle size of 40-80 μm, and 0-30% of particle size greater than 90 μm, 30-50% of particle size less than 45 μm, and not less than 10% of particle size less than 20 μm. As the particle shape of the catalyst, for example, the following can be exemplified: spherical shape, column shape, ring shape, plum blossom shape, and shamrock shape. For example, the catalyst particle has an outer diameter typically of 1-10 mm, and a length generally of 2-10 mm. The catalyst may be commercially available directly or may be produced by any conventional method known in the art.

According to one aspect of the present invention, the type of the ammoxidation reactor is not particularly limited, and for example the following can be specifically exemplified: fixed bed reactor and fluidized bed reactor, preferably fluidized bed reactor. For example, the fluidized bed reactor may include a gas distribution plate, a gas distributor, a cooling water pipe, a cyclone separator, and the like. For this purpose, the oxygen-containing gas or the heating medium can enter the interior of the fluidized bed reactor through the gas distribution plate, and the ammoxidation substrate and/or the ammonia gas can enter the interior of the fluidized bed reactor through the gas distributor. The cooling water pipe can remove excess heat from the reactor, and the cyclone separator can return the gas-entrained catalyst to the lower end of the reactor. Further, the fluidized bed reactor is provided with several monitoring points to measure the temperature and the pressure, and the operation states of the reaction system including the input amount of each of the reaction feedstocks, the heating medium and the like ($Nm^3/h$ or $Nm^3/h/m^2$), the reactor operation line speed, and the like can be directly shown on the DCS control system.

According to one aspect of the present invention, after the end of the preheating process or the preheating step, the launch process of the start-up process of the ammoxidation reaction can be subsequently carried out according to any method and any manner known to those skilled in the art. For this reason, in order to perform the launch process, for example, the following can be exemplified: after the end of said preheating process or the preheating step, each of ammoxidation reaction feedstocks (including the ammonia gas, the oxygen-containing gas and the ammoxidation substrate, particularly including the ammonia gas, air and propylene) are input to the ammoxidation reactor according to any manner and any method known in the art, and according to the requirement, the inputs of these ammoxidation reaction feedstocks to the ammoxidation reactor are adjusted respectively or in combination, until all of the input amounts of these ammoxidation reaction feedstocks to the ammoxidation reactor reach the predetermined values at which the ammoxidation reactor is stably operated.

According to one aspect of the present invention, it also relates to a start-up process of the ammoxidation reaction. It is known in the art that the start-up process of the ammoxidation reaction must include a preheating step and a launch process. Preferably, the preheating step may correspond to the preheating process described above in the present description.

According to one aspect of the present invention, the start-up process of the ammoxidation reaction comprises the following steps:

(1) heating the catalyst bed in the ammoxidation reactor with an oxygen-containing gas (sometimes referred to as a preheating step);

(2) continuously inputting ammonia gas to the ammoxidation reactor;

(3) continuously inputting an ammoxidation substrate to the ammoxidation reactor; and (4) optionally, adjusting the respective input amounts of the oxygen-containing gas, the ammonia gas and the ammoxidation substrate to the ammoxidation reactor to their respective predetermined values.

According to one aspect of the present invention, in the step (1), as the oxygen-containing gas, air can be particularly exemplified.

According to one aspect of the present invention, in the step (1), the reactor operation linear speed of the ammoxidation reactor is 0.03-0.15 m/s, preferably is controlled to be 0.03-0.1 m/s. For this reason, the reactor operation linear speed can be conveniently achieved, for example, by adjusting the input flow rate or the input amount of the heating medium to the ammoxidation reactor and the like. The inventors of the present invention have surprisingly found that by limiting the reactor operation linear speed to the specific range, the launch time of the start-up process of the present invention can be significantly reduced, and correspondingly the consumption amount of the ammoxidation reaction feedstock is also significantly reduced.

According to one aspect of the present invention, in the step (1), the input amount of the heating medium to the ammoxidation reactor is generally 54-276 $Nm^3/h/m^2$, preferably 54-182 $Nm^3/h/m^2$. For this reason, the input amount can be conveniently adjusted, for example, by adjusting the input flow rate of the heating medium to the ammoxidation reactor. The inventors of the present invention have surprisingly found that by limiting the input amount to the specific range, the launch time of the start-up process of the present invention can be significantly reduced, and correspondingly the consumption amount of the ammoxidation reaction feedstock is also significantly reduced.

Without being bound by any theory, the inventors of the present invention believe that by using a lower reactor operation linear speed or a lower input amount of the oxygen-containing gas compared to the prior art, at the end of the preheating step, the total residual amount of the oxygen-containing gas in the ammoxidation reactor is significantly reduced, whereby the total amount of the oxygen-containing gas that needs to be treated (e.g., purged or consumed) in the subsequent launch process is also significantly reduced. For this reason, each of the ammoxidation reaction feedstocks can quickly reach the requirement stipulated by the stable operation of the ammoxidation reactor, resulting in that the consumption amounts of these reaction feedstocks are correspondingly significantly reduced. Moreover, if the operation linear speed or the input amount exceeds the range specified by the present invention, since the amount of oxygen-containing gas entering the reactor is relatively high, a possibility that an incompletely reacted ammonia gas present in the subsequent launch process is instantaneously exposed to a certain concentration of oxygen is not excluded, which may lead to an explosion risk. In addition, if the operation linear speed or the input amount is lower than the range specified by the present invention, the fluidization quality of the catalyst is likely to be poor, so that the reaction process of the ammoxidation reaction feedstocks is insufficient, resulting in that the ratio of the unreacted ammonia gas in the system increases, thereby increasing the risk of explosion accident.

According to one aspect of the present invention, the catalyst bed in the ammoxidation reactor is heated through the step (1) to any temperature which can be expected when the ammoxidation reactor is preheated according to the prior art; for example the following can be specifically exemplified: 360° C. or higher, 370° C. or higher, or 380° C. or higher, or generally 500° C. or lower, 450° C. or lower, 400° C. or lower, or 390° C. or lower; however there is no special limitation in this aspect in the present invention. In addition, the time required or experienced by the step (1) is not limited by the present invention, and said time depends on whether or not each unit of the production plant has possessed the requisite condition of the start-up operation and in general it is also difficult to be pre-estimated. Moreover, as the temperature rise rate of the heating, any numerical value conventionally known in the art can be referred to, but as an example, it is usually 10-100° C./h.

According to one aspect of the present invention, in the step (1), the pressure (gauge pressure) in the ammoxidation reactor is generally 0.030-0.060 MPa, preferably 0.030-0.055 MPa, but sometimes not limited thereto.

According to one aspect of the present invention, the catalyst to be used is not particularly limited, as long as it is any catalyst known in the art to render the ammoxidation substrate, the ammonia gas and the molecular oxygen to carry out the ammoxidation reaction (for example, to form a nitrile compound). As the catalyst, for example, the following can be exemplified: Mo—Bi based/support catalyst, Mo—Fe based/support catalyst, Mo—V based/support catalyst and the like that contain the active element Mo, or Sb—Fe based/support catalyst and the like that contain the active element Sb. One of these catalysts can be used alone, or two or more of them can be used in combination. Herein, as the support, the following can be exemplified: alumina and silica. One of these supports can be used alone, or two or more of them can be used in combination. As the particle size distribution of the catalyst, for example, the following can be exemplified: an average particle size of 40-80 μm, and 0-30% of particle size greater than 90 μm, 30-50% of particle size less than 45 μm, and not less than 10% of particle size less than 20 μm. As the particle shape of the catalyst, for example, the following can be exemplified: spherical shape, column shape, ring shape, plum blossom shape, and shamrock shape. For example, the catalyst particle has an outer diameter typically of 1-10 mm, and a length generally of 2-10 mm. The catalyst may be commercially available directly or may be produced by any conventional method known in the art.

According to one aspect of the present invention, the type of the ammoxidation reactor is not particularly limited, and for example the following can be specifically exemplified: fixed bed reactor and fluidized bed reactor, preferably fluidized bed reactor. For example, the fluidized bed reactor may include a gas distribution plate, a gas distributor, a cooling water pipe, a cyclone separator, and the like. For this purpose, the oxygen-containing gas or the heating medium can enter the interior of the fluidized bed reactor through the gas distribution plate, and the ammoxidation substrate and/or the ammonia gas can enter the interior of the fluidized bed reactor through the gas distributor. The cooling water pipe can remove excess heat from the reactor, and the cyclone separator can return the gas-entrained catalyst to the lower end of the reactor. Further, the fluidized bed reactor is provided with several monitoring points to measure the temperature and the pressure, and the operation states of the reaction system including the input amount of each of the reaction feedstocks, the heating medium and the like ($Nm^3/h$ or $Nm^3/h/m^2$), the reactor operation line speed, and the like can be directly shown on the DCS control system.

According to one aspect of the present invention, after the end of the preheating step of the step (1), the launch process of the ammoxidation reaction can begin. Here, the launch process at least comprises the aforementioned step (2), step (3) and step (4), or covers the whole process starting from step (2) up to the end of the step (4).

According to one aspect of the present invention, in the step (2), the ammonia gas is continuously input to the ammoxidation reactor.

According to one aspect of the present invention, in the step (2), the temperature of the catalyst bed is generally 390° C. or higher, preferably 400° C. or higher, more preferably 400-440° C. After inputting the ammonia gas, the heat released by the ammoxidation reaction causes the temperature in the ammoxidation reactor to rise relative to the temperature before inputting the ammonia gas, and generally can reach the initial temperature at which the ammoxidation substrate undergoes an ammoxidation reaction. In order to avoid a too high temperature, it is sometimes necessary to simultaneously input a certain amount of cooling coils to control the temperature of the catalyst bed during the step (2).

According to one aspect of the present invention, in the step (2), the target value of the input amount of the ammonia gas to the ammoxidation reactor is generally 7.5-110 Nm$^3$/h/m$^2$, 13.7-69.1 Nm$^3$/h/m$^2$ or 7.5-45.6 Nm$^3$/h/m$^2$. In particular, in the case where the ammoxidation substrate is propylene, the target value is generally 7.5-45.6 Nm$^3$/h/m$^2$. As the manner of inputting the ammonia gas, for example, the following can be exemplified: according to any mode or any method conventionally known in the art, it can start from a small dose and gradually increase to the target value (for example, in multiple times, in several steps or successively), or can reach the target value in one step; however there is no special limitation in this aspect in the present invention. In the manner of inputting the ammonia gas of starting from the small dose and gradually increasing to the target value, the damage of an instantaneous large flow amount to the control valve can be avoided, and the statical electricity potentially produced in the pipeline can be reduced in the case of the instantaneous large flow amount.

According to one aspect of the present invention, in the step (2), the ratio of the target value of the input amount of the ammonia gas to the value of the input amount of the oxygen-containing gas is generally 1:2.5-7, preferably 1:4-6.5. For this reason, it will be apparent to those skilled in the art that in order to make the ratio fall in the range specified by the present invention, it is sometimes necessary to correspondingly adjust or control the input amount of the oxygen-containing gas to the ammoxidation reactor according to the requirements, while adjusting or controlling the input amount of the ammonia gas to the ammoxidation reactor. The input amount of the oxygen-containing gas to the ammoxidation reactor in the step (2) is not particularly limited by the present invention, as long as the input amount and the ratio thereof can reach the requirement as specified by the present invention. As required, the input amount of the oxygen-containing gas to the ammoxidation reactor can be also maintained substantially constant throughout the step (2). For the operation convenience, at least at the beginning of the step (2), the input amount of the oxygen-containing gas to the ammoxidation reactor may be a corresponding value that has been reached at the end of the step (1), for example the following can be specifically exemplified: 54-276 Nm$^3$/h/m$^2$. In addition, the term "substantially constant" means that the numerical value remains absolutely constant or the change magnitude of the numerical value is within ±10% (preferably ±5%).

According to one aspect of the present invention, in the step (2), the pressure in the ammoxidation reactor (gauge pressure) is generally 0.030-0.060 MPa, preferably 0.030-0.040 MPa, but sometimes not limited thereto.

According to one aspect of the present invention, in the step (2), the reactor operation linear speed is generally 0.04-0.18 m/s, preferably 0.05-0.15 m/s.

According to one aspect of the present invention, the step (3) begins after the step (2) proceeds for 2-20 minutes. It is preferable that the step (3) begins after the step (2) proceeds for 5-18 minutes. That is to say, for example, the step (3) starts at the time that the step (2) proceeds for 2-20 minutes or the step (2) proceeds for 2-20 minutes to the end, then the step (3) starts; and other similar expressions can be similarly understood. In addition, in the context of the present application invention, for example, the term "end" will be sometimes used with respect to a certain step; the term "end" only represents the absence of the step due to the interfusion into its subsequent step, however does not mean the termination of the operation for conveying the materials involved in said step. Specifically, taking "continuously inputting the ammonia gas to the ammoxidation reactor" involved in the step (2) as an example, the so-called "the end of the step (2)" only represents the absence of the step (2) due to the interfusion into its subsequent step (3) or step (3-1), however the operation of continuously inputting the ammonia gas to the ammoxidation reactor involved in the step (2) still continues in the subsequent step (3) or step (3-1) and is not terminated. Other similar expressions can be similarly understood.

According to one aspect of the present invention, in the step (3), the ammoxidation substrate, in particular propylene, is continuously input to the ammoxidation reactor.

According to one aspect of the present invention, at the beginning of the step (3), from the viewpoint of improving the operation safety or reducing the explosion risk of the reaction mixture in the ammoxidation reactor, for example, because the composition is within the explosion limit range, the content of the molecular oxygen (relative to the total volume of the tail gas) in the reaction tail gas (i.e., the tail gas discharged from the outlet of the ammoxidation reactor) is generally 7.5 vol % or less, preferably 7-7.5 vol %.

According to one aspect of the present invention, the ammonia gas enters the ammoxidation reactor in advance of the ammoxidation substrate (such as propylene). From the MSDS characteristics of the materials, the ammonia gas has a higher explosion lower limit than the ammoxidation substrate; that is to say, in the same oxygen-containing atmosphere, in the concentration range of from zero to the explosion lower limit, the operation process allows the safe operation concentration of the ammonia gas in the system to be obviously higher than the safe operation concentration of the ammoxidation substrate in the system; compared with the entry of the ammoxidation substrate into the reactor before the ammonia gas, the entry of the ammonia gas as the reaction feedstock into the reactor before the ammoxidation substrate, in the start-up process of the plant, reduces the explosion risk and substantially increases the safety factor.

According to one aspect of the present invention, in the step (3), the temperature of the catalyst bed is generally 400-440° C., preferably 400-430° C. or 410-430° C. In order to avoid a too high temperature, it is sometimes necessary to simultaneously input a certain amount of cooling coils to control the temperature of the catalyst bed during the step (3).

According to one aspect of the present invention, in the step (3), the target value of the input amount of the ammoxidation substrate to the ammoxidation reactor is generally 5.2-110.5 Nm$^3$/h/m$^2$, preferably 9.13-65.8 Nm$^3$/h/m$^2$. Here, the respective input amounts of the oxygen-containing gas and the ammonia gas to the ammoxidation reactor or the change mode of the input amount is not particularly limited and can be arbitrarily selected by those skilled in the art according to the circumstances, as long as it is guaranteed that the ammoxidation reaction of these ammoxidation reaction feedstocks at least can be carried out without any explosion risk. Specifically, for example, as the input amount of the oxygen-containing gas to the ammoxidation reactor, for example the following can be specifically exemplified: 44.2-1270.7 Nm$^3$/h/m$^2$, but the present invention is not limited thereto. In addition, specifically, for example, as the input amount of the ammonia gas to the ammoxidation reactor, for example the following can be specifically exemplified: 7.5-110 Nm$^3$/h/m$^2$, but the present invention is not limited thereto.

According to one aspect of the present invention, in the step (3), the pressure in the ammoxidation reactor (gauge pressure) is generally 0.030-0.060 MPa, preferably 0.030-0.045 MPa, but sometimes not limited thereto.

According to one aspect of the present invention, in the step (3), the reactor operation linear speed is generally 0.04-0.32 m/s, preferably 0.05-0.20 m/s or 0.04-0.17 m/s.

According to one aspect of the present invention, from the viewpoint of avoiding the explosion risk, the step (3) at least includes the step (3-1) and the step (3-2).

Step (3-1): while maintaining the input amount of the ammonia gas to the ammoxidation reactor substantially constant, starting to input the ammoxidation substrate to the ammoxidation reactor. Here, the term "substantially constant" means that the numerical value remains absolutely constant or the change magnitude of the numerical value is within ±10% (preferably ±5%). Here, for the operation convenience, the input amount of the ammonia gas to the ammoxidation reactor can be the input amount of the ammonia gas to the ammoxidation reactor at the end of the step (2), and for example is generally 7.5-110 $Nm^3/h/m^2$, 13.7-69.1 $Nm^3/h/m^2$ or 7.5-45.6 $Nm^3/h/m^2$. In particular, in the case where the ammoxidation substrate is propylene, the input amount of the ammonia gas is generally 7.5-45.6 $Nm^3/h/m^2$.

According to one aspect of the present invention, at the beginning of the step (3-1), from the viewpoint of improving the operation safety or reducing the explosion risk of the reaction mixture in the ammoxidation reactor, for example, because the composition is within the explosion limit range, the content of the molecular oxygen (relative to the total volume of the tail gas) in the reaction tail gas (i.e., the tail gas discharged from the outlet of the ammoxidation reactor) is generally 7.5 vol % or less, preferably 7-7.5 vol %.

According to one aspect of the present invention, in the step (3-1), the temperature of the catalyst bed is 400-440° C., 400-430° C. or 400-415° C. In order to avoid a too high temperature, it is sometimes necessary to simultaneously input a certain amount of cooling coils to control the temperature of the catalyst bed during the step (3-1).

According to one aspect of the present invention, in the step (3-1), the pressure in the ammoxidation reactor (gauge pressure) is generally 0.030-0.060 MPa, preferably 0.030-0.040 MPa, but sometimes not limited thereto.

According to one aspect of the present invention, in the step (3-1), the mole ratio of the ammoxidation substrate to ammonia being input to the ammoxidation reactor is generally 1:4-7, preferably is 1:4.5-6.5. The mole ratio can be implemented according to any method and any manner conventionally known in the art, for example, by adjusting the input amount of the ammoxidation substrate to the ammoxidation reactor and the like; however there is no special limitation in this aspect in the present invention.

According to one aspect of the present invention, in the step (3-1), the target value of the input amount of the ammoxidation substrate to the ammoxidation reactor can be 1.5-22.1 $Nm^3/h/m^2$, 2.74-13.8 $Nm^3/h/m^2$ or 1.5-11.4 $Nm^3/h/m^2$. In particular, in the case where the ammoxidation substrate is propylene, the target value of the input amount is generally 1.5-11.4 $Nm^3/h/m^2$. In the case that the ammoxidation substrate (in particular propylene) is input to the ammoxidation reactor, it can start from a small dose and gradually increase to the target value (for example, in multiple times, in several steps or successively), or can reach the target value in one step; however there is no special limitation in this aspect in the present invention. Once the ammoxidation substrate is introduced, the ammoxidation reaction of the substrate also proceeds under the action of a catalyst at the current temperature condition. The rate of the ammoxidation reaction is very high, and more molecular oxygen is consumed during the reaction, so that the molecular oxygen content in the reaction tail gas is further decreased, meanwhile the reaction heat is released. Due to the further reduction of the molecular oxygen content in the ammoxidation reactor, the explosion limit of the reaction product as the combustible material such as acrylonitrile can be avoided, which is also the reason why the low target value (in comparison with the prior art) is used when the ammoxidation substrate is input.

According to one aspect of the present invention, the step (3-2) begins after the step (3-1) proceeds for 2-20 minutes. It is preferable that the step (3-2) begins after the step (3-2) proceeds for 3-18 minutes.

Step (3-2): Adjusting the respective input amounts of the oxygen-containing gas and the ammoxidation substrate to the ammoxidation reactor. Here, as the adjustment, it can be carried out in any manner known in the art. Specifically, for example, the following can be exemplified: the input amount can be changed as a result of changing the flow adjusting device (for example a valve, a flowmeter, an orifice plate or the like) on the pipeline for inputting the oxygen-containing gas and/or the ammoxidation substrate into the ammoxidation reactor. In addition, as the manner of adjusting, for example, the following can be exemplified: it can start from an initial input amount and gradually increase to the corresponding target value (for example, in multiple times, in several steps or successively).

According to one aspect of the present invention, at the beginning of the step (3-2), from the viewpoint of improving the operation safety or reducing the explosion risk of the reaction mixture in the ammoxidation reactor, for example, because the composition is within the explosion limit range, the content of the molecular oxygen (relative to the total volume of the tail gas) in the reaction tail gas is generally 2 vol % or less, preferably 0.5-2 vol %. In addition, from the viewpoint of avoiding the decrease in the catalyst activity, preferably in the whole course of the step (3-2), for example, by adjusting the respective input amounts of the oxygen-containing gas and the ammoxidation substrate to the ammoxidation reactor, the content of the molecular oxygen (relative to the total volume of the tail gas) in the reaction tail gas is therefore maintained in the range of 0.5-2vol % all along.

According to one aspect of the present invention, in the step (3-2), depending on the kind of the ammoxidation substrate, the temperature of the catalyst bed is generally 400-550° C., 420-450° C., 400-440° C. or 425-440° C. In particular, in the case where the ammoxidation substrate is propylene, the temperature is generally 420-450° C., preferably 425-440° C. In order to avoid a too high temperature, it is sometimes necessary to simultaneously input a certain amount of cooling coils to control the temperature of the catalyst bed during the step (3-2).

According to one aspect of the present invention, in the step (3-2), the pressure in the ammoxidation reactor (gauge pressure) is generally 0.030-0.060 MPa, preferably 0.035-0.045 MPa, but sometimes not limited thereto.

According to one aspect of the present invention, in the step (3-2), the respective input amounts of the oxygen-containing gas and the ammoxidation substrate to the ammoxidation reactor are adjusted or gradually increased (for example, in multiple times, in several steps or successively), so that the mole ratio of the ammoxidation substrate to the ammonia gas being input to the ammoxidation reactor (the ammonia gas ratio) and/or the mole ratio of the ammoxidation substrate to the oxygen-containing gas (as the molecular oxygen) (the air ratio) reach the proportional parameters when the plant is normally operated. Depending on the specific size of the reactor and the arrangement of its internal components, the proportional parameters when the plant is normally operated can be varied. Specifically, for example, the ammonia gas ratio is generally 1:0.8-1:5, preferably 1:0.85-1:4.5. Specifically, for example, the air ratio is generally 1:4-1:30, preferably 1:4.5-1:27. Furthermore, for example, in the case where the ammoxidation substrate is propylene, the ammonia gas ratio is generally 1:1-1:1.5, preferably 1:1.05-1:1.3. Furthermore, for example, in the case where the ammoxidation substrate is propylene, the air ratio is generally 1:8.5-1:11.5, preferably 1:9-1:9.8. In addition, it will be apparent to those skilled in the art that in order to make these ratios fall in the range specified by the present invention, it is sometimes necessary to correspondingly adjust or control the input amount of the ammonia gas to the ammoxidation reactor according to the requirements, while adjusting the respective input amounts of the oxygen-containing gas and the ammoxidation substrate to the ammoxidation reactor. The input amount of the ammonia gas to the ammoxidation reactor in the step (2) is not particularly limited by the present invention, as long as these ratios can reach the requirement as specified by the present invention without producing any explosion risk. As required, the input amount of the ammonia gas to the ammoxidation reactor can be also maintained substantially constant throughout the step (3-2). For the operation convenience, at least at the beginning of the step (3-2), the input amount of the ammonia gas to the ammoxidation reactor may be a corresponding numerical value that has been reached at the end of the step (3-1), for example the following can be specifically exemplified: 7.5-110 $Nm^3/h/m^2$ or 7.5-45.6 $Nm^3/h/m^2$. In addition, the term "substantially constant" means that the numerical value remains absolutely constant or the change magnitude of the numerical value is within ±10% (preferably ±5%).

According to one aspect of the present invention, in the step (3-2), the target value of the input amount of the ammoxidation substrate to the ammoxidation reactor is 5.2-110.5 $Nm^3/h/m^2$, preferably 9.13-65.8 $Nm^3/h/m^2$, the target value of the input amount of the oxygen-containing gas to the ammoxidation reactor is 44.2-1270.7 $Nm^3/h/m^2$, preferably 82.17-644.9 $Nm^3/h/m^2$.

According to one aspect of the present invention, the reactor operation linear speed of the step (3-1) is generally 0.04-0.18 m/s, preferably 0.05-0.15 m/s or 0.05-0.15 m/s.

According to one aspect of the present invention, the reactor operation linear speed of the step (3-2) is generally 0.04-0.32 m/s, preferably 0.05-0.2 m/s or 0.04-0.17 m/s.

According to one aspect of the present invention, starting from the viewpoint of the more excellent expected technical effects of the present invention, preferably the reactor operation linear speed of the step (3-1) and the reactor operation linear speed of the step (3-2) are 0.04-0.18 m/s and 0.04-0.32 m/s respectively, preferably 0.05-0.15 m/s and 0.05-0.2 m/s respectively, or 0.05-0.15 m/s and 0.04-0.17 m/s respectively.

According to one aspect of the present invention, the subsequent step begins after the step (3-2) proceeds for 2-30 minutes. Here, as the subsequent step, for example, the step (4) can be exemplified. It is preferable that the subsequent step begins after the step (3-2) proceeds for 5-25 minutes.

According to one aspect of the present invention, the time period from the beginning of the step (3-1) to the end of the step (3-2) is generally 2-50 minutes, preferably 8-43 minutes.

According to one aspect of the present invention, the step (4) begins after the step (3) proceeds for 2-50 minutes. It is preferable that the step (4) begins after the step (3) proceeds for 8-43 minutes.

According to one aspect of the present invention, in the step (4), the respective input amounts of the oxygen-containing gas, the ammonia gas and the ammoxidation substrate to the ammoxidation reactor are adjusted to their respective predetermined values. If the respective input amounts of the oxygen-containing gas, the ammonia gas and the ammoxidation substrate to the ammoxidation reactor have been adjusted to the respective predetermined values through other step(s) before the step (4) such as the step (3) or the step (3-2), this step (4) can be omitted to become an optional step. However, from the viewpoint of the operation safety, the step (4) is preferably present.

According to one aspect of the present invention, in the step (4), the temperature of the catalyst bed is 400-550° C. or 400-440° C., preferably 400-440° C. or 425-440° C. In order to avoid a too high temperature, it is sometimes necessary to simultaneously input a certain amount of cooling coils to control the temperature of the catalyst bed during the step (4).

According to one aspect of the present invention, in the step (4), the pressure in the ammoxidation reactor (gauge pressure) is generally 0.030-0.060 MPa, preferably 0.035-0.055 MPa, but sometimes not limited thereto.

According to one aspect of the present invention, in the step (4), the predetermined value of the input amount of the ammoxidation substrate (in particular propylene) is 110-160 $Nm^3/h/m^2$, preferably 117-143 $Nm^3/h/m^2$. To this end, the input amount of the ammoxidation substrate can be adjusted to the predetermined value according to any manner known in the art. Specifically, for example, the following can be exemplified: the input amount can be changed as a result of changing the flow adjusting device (for example a valve, a flowmeter, an orifice plate or the like) on the pipeline for inputting the ammoxidation substrate into the ammoxidation reactor.

In addition, as the manner of adjusting, for example, the following can be exemplified: it can start from an initial input amount and gradually increase to the corresponding predetermined value (for example, in multiple times, in several steps or successively).

According to one aspect of the present invention, in the step (4), the predetermined value of the input amount of the ammonia gas is 120-230 $Nm^3/h/m^2$, preferably 125-185 $Nm^3/h/m^2$. To this end, the input amount of the ammonia gas can be adjusted to the predetermined value according to any manner known in the art. Specifically, for example, the following can be exemplified: the input amount can be changed as a result of changing the flow adjusting device (for example a valve, a flowmeter, an orifice plate or the like) on the pipeline for inputting the ammonia gas into the ammoxidation reactor. In addition, as the manner of adjusting, for example, the following can be exemplified: it can start from an initial input amount and gradually increase to the corresponding predetermined value (for example, in multiple times, in several steps or successively).

According to one aspect of the present invention, in the step (4), the predetermined value of the input amount of the oxygen-containing gas (in particular air) is 600-1600 $Nm^3/h/m^2$, preferably 1000-1500 $Nm^3/h/m^2$ or 1050-1400 $Nm^3/h/m^2$. To this end, the input amount of the oxygen-containing gas can be adjusted to the predetermined value according to any manner known in the art. Specifically, for example, the following can be exemplified: the input amount can be changed as a result of changing the flow adjusting device (for example a valve, a flowmeter, an orifice plate or the like) on the pipeline for inputting the oxygen-containing gas into the ammoxidation reactor. In addition, as the manner of adjusting, for example, the following can be exemplified: it can start from an initial input amount and gradually increase to the corresponding predetermined value (for example, in multiple times, in several steps or successively).

According to one aspect of the present invention, in the step (4), the reactor operation linear speed is generally 0.5-1.2 m/s, preferably 0.65-0.95 m/s.

According to one aspect of the present invention, the start-up process ends after the step (4) proceeds for 5-30 minutes. It is preferable that the start-up process ends after the step (4) proceeds for 6-25 minutes.

According to one aspect of the present invention, starting from the viewpoint of the more excellent expected technical effects of the present invention, it is preferable that the reactor operation linear speed of the step (1), the reactor operation linear speed of the step (2), the reactor operation linear speed of the step (3) and the reactor operation linear speed of the step (4) respectively are 0.03-0.15 m/s, 0.04-0.18 m/s, 0.04-0.32 m/s and 0.5-1.2 m/s, preferably respectively are 0.03-0.1 m/s, 0.05-0.15 m/s, 0.05-0.20 m/s (or 0.04-0.17 m/s) and 0.65-0.95 m/s.

According to one aspect of the present invention, the time period from the beginning of the step (2) to the end of the start-up process (namely the launch time of the start-up process) is generally 10-100 minutes, preferably 20-60 minutes, more preferably 20-50 minutes.

According to one aspect of the present invention, the parameters such as the reaction temperature, the reaction pressure, the operation linear speed and the like arrive at the predetermined target process parameters with some operation means for adjusting the temperature and adjusting the pressure, for example, the reaction temperature can be adjusted by increasing or decreasing the number of cooling coils. For the fresh catalyst, the catalyst has a relatively strong ammonia-burning ability and therefore needs a domestication process. For the first start-up of the plant using a fresh catalyst, the domestication is run under an operation load that is desirably 70-95%, preferably 80-90% of the full load. For the equilibrium catalyst, the start-up of the plant is not influenced by this factor and can be run under 70-110% of the full load of the plant.

According to one aspect of the present invention, in the start-up process, the various steps are closely coupled to each other for continuous operation (i.e., there is no intermediate paused or suspended operation between different steps).

EXAMPLES

The invention is further illustrated by the following examples, but the invention is not limited to the examples.

In the following examples and comparative examples, it is exemplified that air is used as the heating medium and one of the ammoxidation reaction feedstocks, but the present invention is not limited thereto. In addition, as an example, the temperature of the heating medium is 370-400° C., but the present invention is not limited thereto.

Example 1

The fluidized bed reactor had a diameter of 5.1 meters and a catalyst bed height of 6.5 meters. The catalyst was a Mo—V acrylonitrile fluidized bed catalyst (SANC series, manufactured by Sinopec Shanghai Petrochemical Research Institute). The unreacted ammonia gas in the reaction tail gas was absorbed with sulfuric acid (having a concentration of 98wt %).

The start-up process was as follows:

1. The reaction pressure was 0.3kg/cm$^2$, the input amount of air was adjusted to 100 Nm$^3$/h/m$^2$, or the reactor operation linear speed was adjusted to 0.057 m/s, so that the temperature of the catalyst bed in the reactor reached 380° C.

2. The flow meter for the ammonia gas was adjusted in two runs: firstly, the input amount of the ammonia gas was controlled to be 150 Nm$^3$/h and stabilized for 1.5 minutes, and then the input amount of the ammonia gas was controlled to be 372 Nm$^3$/h, and the reactor operation linear speed was adjusted to be 0.068 m/s. The whole process was completed over 12 minutes.

3. The content of the molecular oxygen in the reaction tail gas was approximately 7.2 vol %. Propane was introduced into the reactor, the input amount of propane was controlled to be 81 Nm$^3$/h, and the reactor operation linear speed was adjusted to be 0.07 m/s. The whole process was completed over 4 minutes.

4. The content of the molecular oxygen in the reaction tail gas was 1.5 vol %. The flowmeter for air and the flowmeter for propane were adjusted synchronously. The input amount of air was controlled to be 2753 Nm$^3$/h. The input amount of propane was controlled to be 286 Nm$^3$/h. The reactor operation linear speed was adjusted to be 0.1 m/s. The whole process was completed over 6 minutes.

5.The flowmeter for propane, the flowmeter for the ammonia gas, and the flowmeter for air were adjusted until the input amount of propane was 2500 Nm$^3$/h, the input amount of the ammonia gas was 3250 Nm$^3$/h, and the input amount of air was 24000 Nm$^3$/h. The reactor operation linear speed was adjusted to be 0.78 m/s. The whole process was completed over 12 minutes.

In each of the above steps, as needed, the reaction temperature can be controlled by adjusting the amount of the water tubes for removing the heat in use. The reaction temperature was 440° C. The reaction pressure (gauge pressure) was 0.050 MPa. The launch time of the start-up process was 34 minutes. The total consumption of the ammonia gas was 786 Nm$^3$. The total consumption of propane was 534 Nm$^3$. The total consumption of sulfuric acid was 172 Kg.

Example 2

The fluidized bed reactor had a diameter of 2.8 meters and a catalyst bed height of 5 meters. The catalyst was a Mo—Fe based hydrocyanic acid fluidized bed catalyst (SANC series, manufactured by Sinopec Shanghai Petrochemical Research Institute). Methanol was introduced in a gaseous form into the reactor after passing through an evaporator and a superheater. The input amount was measured by a volume meter. The unreacted ammonia gas in the reaction tail gas was absorbed with sulfuric acid (having a concentration of 98wt %).

The start-up process was as follows:

1. The reaction pressure was 0.25 kg/cm$^2$, the input amount of air was adjusted to 162 Nm$^3$/h/m$^2$, or the reactor operation linear speed was adjusted to 0.095 m/s, so that the temperature of the catalyst bed in the reactor reached 380° C.

2. The input amount of the ammonia gas was controlled to be 181 Nm³/h, the reactor operation linear speed was adjusted to be 0.11 m/s. The whole process was completed over 10 minutes.

3. The content of the molecular oxygen in the reaction tail gas was approximately 7.2 vol %. Methanol was introduced into the reactor, the input amount of methanol was controlled to be 40 Nm³/h, and the reactor operation linear speed was adjusted to be 0.12 m/s. The whole process was completed over 3 minutes.

4. The content of the molecular oxygen in the reaction tail gas was controlled to be 1.5 vol %. The flowmeter for air and the flowmeter for methanol were adjusted synchronously. The input amount of air was controlled to be 1515 Nm³/h. The input amount of methanol was controlled to be 202 Nm³/h. The reactor operation linear speed was adjusted to be 0.17 m/s. The whole process was completed over 6 minutes.

5. The flowmeter for methanol, the flowmeter for the ammonia gas, and the flowmeter for air were adjusted until the input amount of methanol was 800 Nm³/h, the input amount of the ammonia gas was 720 Nm³/h, and the input amount of air was 6000 Nm³/h. The reactor operation linear speed was adjusted to be 0.66 m/s. The whole process was completed over 12 minutes.

In each of the above steps, as needed, the reaction temperature can be controlled by adjusting the amount of the water tubes for removing the heat in use. The reaction temperature was 440° C. The reaction pressure (gauge pressure) was 0.050 MPa. The launch time of the start-up process was 30 minutes. The total consumption of the ammonia gas was 198 Nm³. The total consumption of methanol was 255 kg. The total consumption of sulfuric acid was 43 Kg.

Example 3

The fluidized bed reactor had a diameter of 2.8 meters and a catalyst bed height of 6.5 meters. The catalyst was a Mo—Bi based acetonitrile fluidized bed catalyst (MB series, manufactured by Sinopec Shanghai Petrochemical Research Institute). Acetic Acid was introduced in a gaseous form into the reactor after passing through an evaporator and a super-heater. The input amount was measured by a volume meter. The unreacted ammonia gas in the reaction tail gas was absorbed with sulfuric acid (having a concentration of 98wt %).

The start-up process was as follows:

1. The reaction pressure was 0.3 kg/cm², the input amount of air was adjusted to 162 Nm³/h/m², or the reactor operation linear speed was adjusted to 0.091 m/s, so that the temperature of the catalyst bed in the reactor reached 380° C.

2. The input amount of the ammonia gas was controlled to be 200 Nm³/h, the reactor operation linear speed was adjusted to be 0.11 m/s. The whole process was completed over 14 minutes.

3. The content of the molecular oxygen in the reaction tail gas was approximately 7.5 vol %.

Acetic acid was introduced into the reactor, the input amount of acetic acid was controlled to be 44 Nm³/h, and the reactor operation linear speed was adjusted to be 0.12 m/s. The whole process was completed over 5 minutes.

4. The content of the molecular oxygen in the reaction tail gas was 1.5 vol %. The flowmeter for air and the flowmeter for acetic acid were adjusted synchronously. The input amount of air was controlled to be 625 Nm³/h. The input amount of acetic acid was controlled to be 125 Nm³/h. The reactor operation linear speed was adjusted to be 0.13 m/s. The whole process was completed over 5 minutes.

5. The flowmeter for acetic acid, the flowmeter for the ammonia gas, and the flowmeter for air were adjusted until the input amount of acetic acid was 800 Nm³/h, the input amount of the ammonia gas was 1280 Nm³/h, and the input amount of air was 4000 Nm³/h. The reactor operation linear speed was adjusted to be 0.52 m/s. The whole process was completed over 12 minutes.

In each of the above steps, as needed, the reaction temperature can be controlled by adjusting the amount of the water tubes for removing the heat in use. The reaction temperature was 400° C. The reaction pressure (gauge pressure) was 0.050 MPa. The launch time of the start-up process was 36 minutes. The total consumption of the ammonia gas was 336 Nm³. The total consumption of acetic acid was 466 kg. The total consumption of sulfuric acid was 73 Kg.

Example 4

The fluidized bed reactor had a diameter of 5.1 meters and a catalyst bed height of 7.3 meters. The catalyst was a Mo—Bi based benzonitrile fluidized bed catalyst (BN series, manufactured by Sinopec Shanghai Petrochemical Research Institute). Toluene was introduced in a gaseous form into the reactor after passing through an evaporator and a super-heater. The input amount was measured by a volume meter. The unreacted ammonia gas in the reaction tail gas was absorbed with sulfuric acid (having a concentration of 98 wt %).

The start-up process was as follows:

1. The reaction pressure was 0.3 kg/cm², the input amount of air was adjusted to 100 Nm³/h/m², or the reactor operation linear speed was adjusted to 0.057 m/s, so that the temperature of the catalyst bed in the reactor reached 380° C.

2. The flow meter for the ammonia gas was adjusted in two runs: firstly, the input amount of the ammonia gas was controlled to be 150 Nm³/h and stabilized for 1.5 minutes, and then the input amount of the ammonia gas was controlled to be 372 Nm³/h, and the reactor operation linear speed was adjusted to be 0.068 m/s. The whole process was completed over 14 minutes.

3. The content of the molecular oxygen in the reaction tail gas was approximately 7.2 vol %. Toluene was introduced into the reactor, the input amount of toluene was controlled to be 41 Nm³/h, and the reactor operation linear speed was adjusted to be 0.07 m/s. The whole process was completed over 5 minutes.

4. The content of the molecular oxygen in the reaction tail gas was 1.5 vol %. The flowmeter for air and the flowmeter for toluene were adjusted synchronously. The input amount of air was controlled to be 2330 Nm³/h. The input amount of toluene was controlled to be 93 Nm³/h. The reactor operation linear speed was adjusted to be 0.077 m/s. The whole process was completed over 6 minutes.

5. The flowmeter for toluene, the flowmeter for the ammonia gas, and the flowmeter for air were adjusted until the input amount of toluene was 1000 Nm³/h, the input amount of the ammonia gas was 4000 Nm³/h, and the input amount of air was 25000 Nm³/h. The reactor operation linear speed was adjusted to be 0.74 m/s. The whole process was completed over 12 minutes.

In each of the above steps, as needed, the reaction temperature can be controlled by adjusting the amount of the water tubes for removing the heat in use. The reaction temperature was 400° C. The reaction pressure (gauge pressure) was 0.045 MPa. The launch time of the start-up process was 37 minutes. The total consumption of the ammonia gas was 755 Nm³. The total consumption of toluene was 2208 kg. The total consumption of sulfuric acid was 165 Kg.

Example 5

The fluidized bed reactor had a diameter of 7.5 meters and a catalyst bed height of 7 meters. The catalyst was a fresh Mo—Bi system acrylonitrile catalyst (SANC series, manufactured by Sinopec Shanghai Petrochemical Research Institute). The unreacted ammonia gas in the reaction tail gas was absorbed with sulfuric acid (having a concentration of 98 wt %).

The start-up process was as follows:

1. The reaction pressure was 0.3 kg/cm², the input amount of air was adjusted to 54 Nm³/h/m², or the reactor operation linear speed was adjusted to 0.030 m/s, so that the temperature of the catalyst bed in the reactor reached 370° C.

2. The flow meter for the ammonia gas was adjusted in two runs: firstly, the input amount of the ammonia gas was controlled to be 150 Nm³/h and stabilized for 1.5 minutes, and then the input amount of the ammonia gas was controlled to be 480 Nm³/h, and the reactor operation linear speed was adjusted to be 0.040 m/s. The whole process was completed over 10 minutes.

3. The content of the molecular oxygen in the reaction tail gas was approximately 7.2 vol %. propylene was introduced into the reactor, the flowmeter for propylene was adjusted so that the input amount of propylene was controlled to be 104 Nm³/h, and the reactor operation linear speed was adjusted to be 0.040 m/s. The whole process was completed over 3 minutes.

4. The content of the molecular oxygen in the reaction tail gas was 1.5 vol %. The flowmeter for air and the flowmeter for propylene were adjusted synchronously. The input amount of air was controlled to be 3686 Nm³/h. The input amount of propylene was controlled to be 384 Nm³/h. The reactor operation linear speed was adjusted to be 0.058 m/s. The whole process was completed over 4 minutes.

5. The flowmeter for propylene, the flowmeter for the ammonia gas, and the flowmeter for air were adjusted until the input amount of propylene was 4861 Nm³/h, the input amount of the ammonia gas was 6076 Nm³/h, and the input amount of air was 46665 Nm³/h. The reactor operation linear speed was adjusted to be 0.7 m/s. The whole process was completed over 10 minutes.

In each of the above steps, as needed, the reaction temperature can be controlled by adjusting the amount of the water tubes for removing the heat in use. The reaction temperature was 425° C. The reaction pressure (gauge pressure) was 0.045 MPa. The launch time of the start-up process was 27 minutes. The total consumption of the ammonia gas was 1092 Nm³. The total consumption of propylene was 835 Nm³. The total consumption of sulfuric acid was 239 Kg.

Example 6

The fluidized bed reactor had a diameter of 7.5 meters and a catalyst bed height of 7 meters. The catalyst was a balanced Mo—Bi system acrylonitrile catalyst (SANC series, manufactured by Sinopec Shanghai Petrochemical Research Institute). The unreacted ammonia gas in the reaction tail gas was absorbed with sulfuric acid (having a concentration of 98 wt %).

The start-up process was as follows:

1. The reaction pressure was 0.3 kg/cm², the input amount of air was adjusted to 59 Nm³/h/m², or the reactor operation linear speed was adjusted to 0.034 m/s, so that the temperature of the catalyst bed in the reactor reached 390° C.

2. The flow meter for the ammonia gas was adjusted in two runs: firstly, the input amount of the ammonia gas was controlled to be 150 Nm³/h and stabilized for 1.5 minutes, and then the input amount of the ammonia gas was controlled to be 577 Nm³/h, and the reactor operation linear speed was adjusted to be 0.041 m/s. The whole process was completed over 11 minutes.

3. The content of the molecular oxygen in the reaction tail gas was approximately 7.3 vol %. Propylene was introduced into the reactor, the flowmeter for propylene was adjusted so that the input amount of propylene was controlled to be 137 Nm³/h, and the reactor operation linear speed was adjusted to be 0.044 m/s. The whole process was completed over 4 minutes.

4. The content of the molecular oxygen in the reaction tail gas was 2.0 vol %. The flowmeter for air and the flowmeter for propylene were adjusted synchronously. The input amount of air was controlled to be 4620 Nm³/h. The input amount of propylene was controlled to be 480 Nm³/h. The reactor operation linear speed was adjusted to be 0.074 m/s. The whole process was completed over 5 minutes.

5. The flowmeter for propylene, the flowmeter for the ammonia gas, and the flowmeter for air were adjusted until the input amount of propylene was 5684 Nm³/h, the input amount of the ammonia gas was 7390 Nm³/h, and the input amount of air was 54000 Nm³/h. The reactor operation linear speed was adjusted to be 0.81 m/s. The whole process was completed over 12 minutes.

In each of the above steps, as needed, the reaction temperature can be controlled by adjusting the amount of the water tubes for removing the heat in use. The reaction temperature was 435° C. The reaction pressure (gauge pressure) was 0.045 MPa. The launch time of the start-up process was 32 minutes. The total consumption of the ammonia gas was 1642 Nm³. The total consumption of propylene was 1160 Nm³. The total consumption of sulfuric acid was 346 Kg.

Example 7

The same procedure as that of Example 6 was carried out except for the following modification.

The start-up process was as follows:

1. The reaction pressure was 0.3 kg/cm², the input amount of air was adjusted to 158 Nm³/h/m², or the reactor operation linear speed was adjusted to 0.091 m/s, so that the temperature of the catalyst bed in the reactor reached 390° C.

2. The flow meter for the ammonia gas was adjusted in two runs: firstly, the input amount of the ammonia gas was controlled to be 180 Nm³/h and stabilized for 1.5 minutes, and then the input amount of the ammonia gas was controlled to be 1166 Nm³/h, and the reactor operation linear speed was adjusted to be 0.11 m/s. The whole process was completed over 9 minutes.

3. The content of the molecular oxygen in the reaction tail gas was approximately 7.5 vol %. Propylene was introduced into the reactor, the flowmeter for propylene was adjusted in two runs: firstly, the input amount of propylene was controlled to be 100 Nm³/h and stabilized for 1.0 minute, and then the input amount of propylene was controlled to be 259 Nm³/h, and the reactor operation linear speed was adjusted to be 0.11 m/s. The whole process was completed over 6 minutes.

4. The content of the molecular oxygen in the reaction tail gas was 1.8 vol %. The flowmeter for air and the flowmeter for propylene were adjusted synchronously. The input amount of air was controlled to be 8960 Nm³/h. The input amount of propylene was controlled to be 933 Nm³/h. The reactor operation linear speed was adjusted to be 0.14 m/s. The whole process was completed over 6 minutes.

5. The flowmeter for propylene, the flowmeter for the ammonia gas, and the flowmeter for air were adjusted until the input amount of propylene was 5684 Nm³/h, the input amount of the ammonia gas was 7105 Nm³/h, and the input amount of air was 54570 Nm³/h. The reactor operation linear speed was adjusted to be 0.81 m/s. The whole process was completed over 15 minutes.

In each of the above steps, as needed, the reaction temperature can be controlled by adjusting the amount of the water tubes for removing the heat in use. The reaction temperature was 430° C. The reaction pressure (gauge pressure) was 0.045 MPa. The launch time of the start-up process was 36 minutes. The total consumption of the ammonia gas was 2150 Nm³. The total consumption of propylene was 1520 Nm³. The total consumption of sulfuric acid was 470 Kg.

Example 8

The same procedure as that of Example 5 was carried out except for the following modification.

The start-up process was as follows:

1. The reaction pressure was 0.3 kg/cm², the input amount of air was adjusted to 181 Nm³/h/m², or the reactor operation linear speed was adjusted to 0.1 m/s, so that the temperature of the catalyst bed in the reactor reached 370° C.

2. The flow meter for the ammonia gas was adjusted in two runs: firstly, the input amount of the ammonia gas was controlled to be 180 Nm³/h and stabilized for 1.5 minutes, and then the input amount of the ammonia gas was controlled to be 1595 Nm³/h, and the reactor operation linear speed was adjusted to be 0.12 m/s. The whole process was completed over 14 minutes.

3. The content of the molecular oxygen in the reaction tail gas was approximately 7.5 vol %.

Propylene was introduced into the reactor, the flowmeter for propylene was adjusted so that the input amount of propylene was controlled to be 354 Nm³/h, and the reactor operation linear speed was adjusted to be 0.13 m/s. The whole process was completed over 7 minutes.

4. The content of the molecular oxygen in the reaction tail gas was 1.8 vol %. The flowmeter for air and the flowmeter for propylene were adjusted synchronously. The input amount of air was controlled to be 11780 Nm³/h. The input amount of propylene was controlled to be 1227 Nm³/h. The reactor operation linear speed was adjusted to be 0.20 m/s. The whole process was completed over 7 minutes.

5. The flowmeter for propylene, the flowmeter for the ammonia gas, and the flowmeter for air were adjusted until the input amount of propylene was 5684 Nm³/h, the input amount of the ammonia gas was 7105 Nm³/h, and the input amount of air was 54570 Nm³/h. The reactor operation linear speed was adjusted to be 0.81 m/s. The whole process was completed over 15 minutes.

In each of the above steps, as needed, the reaction temperature can be controlled by adjusting the amount of the water tubes for removing the heat in use. The reaction temperature was 430° C. The reaction pressure (gauge pressure) was 0.045 MPa. The launch time of the start-up process was 43 minutes. The total consumption of the ammonia gas was 2510 Nm³. The total consumption of propylene was 1594 Nm³. The total consumption of sulfuric acid was 542 Kg.

Comparative Example 1

The same procedure as that of Example 5 was carried out except for the following modification.

The start-up process was as follows:

1. The reaction pressure was 0.3 kg/cm², the input amount of air was adjusted to 323 Nm³/h/m², or the reactor operation linear speed was adjusted to 0.18 m/s, so that the temperature of the catalyst bed in the reactor reached 370° C.

2. The flow meter for the ammonia gas was adjusted in two runs: firstly, the input amount of the ammonia gas was controlled to be 150 Nm³/h and stabilized for 1.5 minutes, and then the input amount of the ammonia gas was controlled to be 300 Nm³/h, and the reactor operation linear speed was adjusted to be 0.21 m/s. The whole process was completed over 10 minutes. At the end of 2, the content of the molecular oxygen in the reaction tail gas was 10.0 vol %, and there was a risk of exceeding the explosion limit of acrylonitrile. Therefore, the start-up process could not proceed any more.

Comparative Example 2

The same procedure as that of Example 5 was carried out except for the following modification.

The start-up process was as follows:

1. The reaction pressure was 0.3 kg/cm², the input amount of air was adjusted to 543 Nm³/h/m², or the reactor operation linear speed was adjusted to 0.3 m/s, so that the temperature of the catalyst bed in the reactor reached 370° C.

2. The flow meter for the ammonia gas was adjusted in two runs: firstly, the input amount of the ammonia gas was controlled to be 300 Nm³/h and stabilized for 1.5 minutes, and then the input amount of the ammonia gas was controlled to be 4800 Nm³/h, and the reactor operation linear speed was adjusted to be 0.38 m/s. The whole process was completed over 45 minutes.

3. The content of the molecular oxygen in the reaction tail gas was approximately 7.2 vol %. Propylene was introduced into the reactor, the flowmeter for propylene was adjusted in two runs: firstly, the input amount of propylene was controlled to be 300 Nm³/h and stabilized for 1.0 minute, and then the input amount of propylene was controlled to be 1043 Nm³/h, and the reactor operation linear speed was adjusted to be 0.39 m/s. The whole process was completed over 21 minutes.

4. The content of the molecular oxygen in the reaction tail gas was 1.5 vol %. The flowmeter for air and the flowmeter for propylene were adjusted synchronously. The input amount of air was controlled to be 36864 Nm³/h. The input amount of propylene was controlled to be 3840 Nm³/h. The reactor operation linear speed was adjusted to be 0.58 m/s. The whole process was completed over 28 minutes.

5. The flowmeter for propylene, the flowmeter for the ammonia gas, and the flowmeter for air were adjusted until the input amount of propylene was 5680 Nm³/h, the input amount of the ammonia gas was 7100 Nm³/h, and the input amount of air was 54570 Nm³/h. The reactor operation linear speed was adjusted to be 0.83 m/s. The whole process was completed over 32 minutes.

In each of the above steps, as needed, the reaction temperature can be controlled by adjusting the amount of the water tubes for removing the heat in use. The reaction temperature was 425° C. The reaction pressure (gauge pressure) was 0.045 MPa. The launch time of the start-up process was 126 minutes. The total consumption of the ammonia gas was 11200 Nm³. The total consumption of propylene was 5000 Nm³. The total consumption of sulfuric acid was 2460 Kg.

The invention claimed is:

1. A preheating process for ammoxidation reaction, comprising:
    feeding a heating medium into an ammoxidation reactor to heat a catalyst bed in the ammoxidation reactor at a linear velocity of 0.03-0.15 m/s, and/or, an input amount of the heating medium of 54-276 Nm³/h/m² .

2. The preheating process according to claim 1, wherein the catalyst bed is heated to a temperature in a range of 360° C. to or 500° C., inclusive.

3. A start-up process for ammoxidation reaction, comprising:
    (1) heating a catalyst bed in an ammoxidation reactor with an oxygen-containing gas at a reactor operation linear velocity of 0.03-0.15 m/s, and/or, an input amount of 54-276 Nm³/h/m² ;
    (2) continuously inputting ammonia gas to the ammoxidation reactor;
    (3) continuously inputting an ammoxidation substrate to the ammoxidation reactor; and
    (4) optionally, adjusting input amounts of the oxygen-containing gas, the ammonia gas, and the ammoxidation substrate to the ammoxidation reactor to respective predetermined values thereof.

4. A start-up process for the ammoxidation reaction, which comprising:
    (1) heating a catalyst bed in an ammoxidation reactor with an oxygen-containing gas;
    (2) continuously inputting an ammonia gas to the ammoxidation reactor;
    (3) continuously inputting an ammoxidation substrate to the ammoxidation reactor; and
    (4) adjusting the respective input amounts of the oxygen-containing gas, the ammonia gas, and the ammoxidation substrate to the ammoxidation reactor to respective predetermined values thereof,
    wherein the reactor operation linear velocity of the oxygen-containing gas in the step (1) is 0.03-0.15 m/s, the reactor operation linear velocity in the step (2) is 0.04-0.18 m/s, and the reactor operation linear velocity in the step (3) 0.04-0.32 m/s, and the reactor operation linear velocity in the step (4) respectively is 0.5-1.2 m/s.

5. The start-up process according to claim 4, wherein in the step (1), the input amount of the oxygen-containing gas to the ammoxidation reactor is 54-276 Nm³/h/m².

6. The start-up process according to claim 3, wherein the ammoxidation substrate is is selected from propane, isobutane, propylene, isobutylene, methanol, ethanol, propanol, dimethyl ether, methyl ethyl ether, acetic acid, methyl acetate, and mixtures thereof.

7. The start-up process according to claim 3, wherein in the step (1), a temperature of the catalyst bed is in a range of 360° C. to 500° C., inclusive, or higher, and/or, in the step (2), the temperature of the catalyst bed is 390° C. or higher, and/or, in the step (3), the temperature of the catalyst bed is 400-440° C., and/or, in the step (4), the temperature of the catalyst bed is 400-550° C.

8. The start-up process according to claim 3, wherein after the step (2) proceeds for 2-20 minutes, the step (3) begins, and/or, after the step (3) proceeds for 2-50 minutes, the step (4) begins, and/or, after the step (4) proceeds for 5-30 minutes, the start-up process ends, and/or, the time period from the beginning of the step (2) to the end of the start-up process is 10-100 minutes.

9. The start-up process according to claim 3, wherein in the step (2), the predetermined value of the input amount of the ammonia gas to the ammoxidation reactor is 7.5-110 Nm³/h/m², and a molar ratio of the predetermined value of the input amount of the ammonia gas to the predetermined value of the input amount of the oxygen-containing gas is 1:2.5-7, and/or, in the step (3), the predetermined value of the input amount of the ammoxidation substrate to the ammoxidation reactor is 5.2-110.5 Nm³/h/m², and/or, in the step (4), the predetermined value of the input amount of the ammoxidation substrate is 110-160 Nm³/h/m², the predetermined value of the input amount of the ammonia gas is 120-230 Nm³/h/m², the predetermined value of the input amount of the oxygen-containing gas is 600-1600 Nm³/h/m².

10. The start-up process according to claim 3, wherein the step (3) comprises:
    (3-1) while keeping the input amount of the ammonia gas to the ammoxidation reactor substantially constant, starting to input the ammoxidation substrate to the ammoxidation reactor; and
    (3-2) regulating the respective input amounts amount of the oxygen-containing gas and the input amount of the ammoxidation substrate to the ammoxidation reactor, wherein the reactor operation linear velocity in the step (3-1) is 0.04-0.18 m/s, and the reactor operation linear velocity in the step (3-2) is 0.04-0.32m/s.

11. The start-up process according to claim 10, wherein the step (3-2) begins after the step (3-1) have proceeded for 2-20 minutes, and/or, a following step begins after the step (3-2) have proceed for 2-30 minutes, and/or, a time period from the beginning of the step (3-1) to the end of the step (3-2) is 2-50 minutes.

12. The start-up process according to claim 10, wherein in the step (3-1), the temperature of the catalyst bed is 400-440° C., and/or, in the step (3-2), the temperature of the catalyst bed is 400-550° C.

13. The start-up process according to claim 10, wherein in the step (3-1), the input amount of the ammoxidation substrate to the ammoxidation reactor is such that a molar ratio of the ammoxidation substrate to the ammonia gas being input to the ammoxidation reactor ranges from 1:4-1:7, and/or, in the step (3-2), the input amount of the oxygen-containing gas and the input amount of the ammoxidation substrate to the ammoxidation reactor are regulated so that the molar ratio of the ammoxidation substrate to the ammonia gas being input to the ammoxidation reactor ranges from 1:0.8-1:5, and the molar ratio of the ammoxidation substrate to the oxygen-containing gas (as the molecular oxygen) being input to the ammoxidation reactor reaches from 1:4-1:30.

14. The start-up process according to claim 10, wherein in the step (3-1), the predetermined value of the input amount of the ammoxidation substrate to the ammoxidation reactor is 1.5-22.1 Nm³/h/m², and/or, in the step (3-2), the predetermined value of the input amount of the ammoxidation substrate to the ammoxidation reactor is 5.2-110.5 $Nm^3/h/m^2$, the predetermined value of the input amount of the oxygen-containing gas to the ammoxidation reactor is 44.2-1270.7 $Nm^3/h/m^2$.

15. The start-up process according to claim 3, wherein at the beginning of the step (3) or at the beginning of the step (3-1), a content of the molecular oxygen in a reaction tail gas (relative to the total volume of the reaction tail gas) is 7.5 vol % or less, and/or, at the beginning of the step (3-2), the content of the molecular oxygen in the reaction tail gas (relative to the total volume of the reaction tail gas) is 2 vol % or less.

16. The start-up process according to claim 4, wherein the ammoxidation substrate is selected from propane, isobutane, propylene, isobutylene, methanol, ethanol, propanol, dimethyl ether, methyl ethyl ether, acetic acid, methyl acetate, and mixtures thereof.

17. The start-up process according to claim 4, wherein in the step (1), a temperature of the catalyst bed ranges from 360° C. to 500° C., inclusive, and/or, in the step (2), the temperature of the catalyst bed is 390° C. or higher, and/or, in the step (3), the temperature of the catalyst bed is 400-440° C., and/or, in the step (4), the temperature of the catalyst bed is 400-550° C.

18. The start-up process according to claim 4, wherein after the step (2) has proceeded for 2-20 minutes, the step (3) begins, and/or, after the step (3) has proceeded for 2-50 minutes, the step (4) begins, and/or, after the step (4) proceeds for 5-30 minutes, the start-up process ends, and/or, the time period from the beginning of the step (2) to the end of the start-up process is 10-100 minutes.

19. The start-up process according to claim 4, wherein in the step (2), the predetermined value of the input amount of the ammonia gas to the ammoxidation reactor is 7.5-110 $Nm^3/h/m^2$, and a molar ratio of the predetermined value of the input amount of the ammonia gas to the predetermined value of the input amount of the oxygen-containing gas is 1:2.5-1:7, and/or, in the step (3), the predetermined value of the input amount of the ammoxidation substrate to the ammoxidation reactor is 5.2-110.5 $Nm^3/h/m^2$, and/or, in the step (4), the predetermined value of the input amount of the ammoxidation substrate is 110-160 $Nm^3/h/m^2$, the predetermined value of the input amount of the ammonia gas is 120-230 $Nm^3/h/m^2$, the predetermined value of the input amount of the oxygen-containing gas is 600-1600 $Nm^3/h/m^2$.

20. The start-up process according to claim 4, wherein the step (3) comprises:
 (3-1) while keeping the input amount of the ammonia gas to the ammoxidation reactor substantially constant, starting to input the ammoxidation substrate to the ammoxidation reactor; and
 (3-2) regulating the input amount of the oxygen-containing gas and the input amount of the ammoxidation substrate to the ammoxidation reactor, wherein the reactor operation linear velocity of the step (3-1) is 0.04-0.18 m/s and the reactor operation linear velocity of the step (3-2) is 0.04-0.32 m/s.

21. The start-up process according to claim 20, wherein the step (3-2) begins after the step (3-1) has proceeded for 2-20 minutes, and/or, a next step begins after the step (3-2) has proceeded for 2-30 minutes, and/or, the time period from the beginning of the step (3-1) to the end of the step (3-2) is 2-50 minutes.

22. The start-up process according to claim 20, wherein in the step (3-1), the temperature of the catalyst bed is 400-440° C., and/or, in the step (3-2), the temperature of the catalyst bed is 400-550° C.

23. The start-up process according to claim 20, wherein in the step (3-1), the input amount of the ammoxidation substrate to the ammoxidation reactor is such an amount that a molar ratio of the ammoxidation substrate to the ammonia gas being input to the ammoxidation reactor ranges from 1:4-1:7, and/or, in the step (3-2), the input amount of the oxygen-containing gas and the input amount of the ammoxidation substrate to the ammoxidation reactor are regulated so that the molar ratio of the ammoxidation substrate to the ammonia gas being input to the ammoxidation reactor ranges from 1:0.8-1:5, and the molar ratio of the ammoxidation substrate to the oxygen-containing gas (as the molecular oxygen) being input to the ammoxidation reactor ranges from 1:4-1:30.

24. The start-up process according to claim 20, wherein in the step (3-1), the predetermined value of the input amount of the ammoxidation substrate to the ammoxidation reactor is 1.5-22.1 $Nm^3/h/m^2$, and/or, in the step (3-2), the predetermined value of the input amount of the ammoxidation substrate to the ammoxidation reactor is 5.2-110.5 $Nm^3/h/m^2$, the predetermined value of the input amount of the oxygen-containing gas to the ammoxidation reactor is 44.2-1270.7 $Nm^3/h/m^2$.

25. The start-up process according to claim 4, wherein at the beginning of the step (3) or at the beginning of the step (3-1), a content of the molecular oxygen in a reaction tail gas (relative to a total volume of the reaction tail gas) is 7.5 vol % or less, and/or, at the beginning of the step (3-2), the content of the molecular oxygen in the reaction tail gas (relative to the total volume of the reaction tail gas) is 2 vol % or less.

26. The start-up process according to claim 10, wherein at the beginning of the step (3) or at the beginning of the step (3-1), a content of the molecular oxygen in a reaction tail gas (relative to the total volume of the reaction tail gas) is 7.5 vol % or less, and/or, at the beginning of the step (3-2), the content of the molecular oxygen in the reaction tail gas (relative to the total volume of the reaction tail gas) is 2 vol % or less.

27. The preheating process according to claim 1, wherein the heating medium is air, the ammoxidation reactor is a fluidized bed reactor, the reactor operation linear velocity is 0.03-0.1 m/s, and/or, the input amount of the heating medium to the ammoxidation reactor is 54-182 $Nm^3/h/m^2$.

28. The start-up process according to claim 3, wherein the ammoxidation reactor is a fluidized bed reactor, wherein the oxygen-containing gas is air, wherein the reactor operation linear velocity is 0.03-0.1 m/s, and the input amount of the oxygen-containing gas to the ammoxidation reactor is 54-182 $Nm^3/h/m^2$.

29. The start-up process according to claim 4, wherein the ammoxidation reactor is a fluidized bed reactor, wherein the oxygen-containing gas is air, wherein the reactor operation linear velocity of the oxygen-containing gas in the step (1) is 0.03-0.1 m/s, the reactor operation linear velocity in the step (2) is 0.05-0.15 m/s, and the reactor operation linear velocity in the step (3) 0.04-0.17 m/s, and the reactor operation linear velocity in the step (4) respectively is 0.65-0.95 m/s.

30. The start-up process according to claim 5, wherein the input amount of the oxygen-containing gas to the ammoxidation reactor is 54-182 $Nm^3/h/m^2$.

31. The start-up process according to claim 7, wherein in the step (1), the temperature of the catalyst bed is in the range of 380° C. to 400° C., inclusive 380° C., and/or, wherein in the step (2), the temperature of the catalyst bed is 400-440° C., and/or, in the step (3), the temperature of the catalyst bed is 410-430° C., and/or, in the step (4), the temperature of the catalyst bed is 425-440° C.

32. The start-up process according to claim 8, wherein after the step (2) proceeds for 5-18 minutes, the step (3) begins, and/or, after the step (3) proceeds for 8-43 minutes, the step (4) begins, and/or, after the step (4) proceeds for 6-25 minutes, the start-up process ends, and/or, the time period from the beginning of the step (2) to the end of the start-up process is 20-50 minutes.

33. The start-up process according to claim 9, wherein in the step (2), the predetermined value of the input amount of the ammonia gas to the ammoxidation reactor is 7.5-45.6 $Nm^3/h/m^2$, and the molar ratio of the predetermined value of the input amount of the ammonia gas to the predetermined value of the input amount of the oxygen-containing gas ranges from 1:4-1:7, and/or, in the step (3), the predetermined value of the input amount of the ammoxidation substrate to the ammoxidation reactor is 9.13-65.8 $Nm^3/h/m^2$, and/or, in the step (4), the predetermined value of the input amount of the ammoxidation substrate is 117-143 $Nm^3/h/m^2$, the predetermined value of the input amount of the ammonia gas is 125-185 $Nm^3/h/m^2$, the predetermined value of the input amount of the oxygen-containing gas is 1050-1400 $Nm^3/h/m^2$, and the oxygen-containing gas is air.

34. The start-up process according to claim 10, wherein the step (3-2) comprises increasing the input amounts of the oxygen-containing gas and the ammoxidation substrate to the ammoxidation reactor, wherein, the reactor operation linear velocity in the step (3-1) is 0.05-0.15 m/s, and the reactor operation linear velocity in the step (3-2) is 0.04-0.17 m/s.

35. The start-up process according to claim 11, wherein the step (3-2) begins after the step (3-1) has proceeded for 3-18 minutes, and/or, the step (4) has proceeded after the step (3-2) proceeds for 5-25 minutes, and/or, the time period from the beginning of the step (3-1) to the end of the step (3-2) is 8-43 minutes.

36. The start-up process according to claim 12, wherein in the step (3-1), the temperature of the catalyst bed is 400-415° C., and/or, in the step (3-2), the temperature of the catalyst bed is 425-440° C.

37. The start-up process according to claim 13, wherein in the step (3-1), the input amount of the ammoxidation substrate to the ammoxidation reactor is such an amount that the molar ratio of the ammoxidation substrate to the ammonia gas being input to the ammoxidation reactor ranges from 1:4.5-1:6.5, and/or, in the step (3-2), the input amount of the oxygen-containing gas and the input amount of the ammoxidation substrate to the ammoxidation reactor are increased so that the molar ratio of the ammoxidation substrate to the ammonia gas being input to the ammoxidation reactor ranges from 1:1.05-1:1.3, and the molar ratio of the ammoxidation substrate to air, as the molecular oxygen, being input to the ammoxidation reactor ranges from 1:9-1:9.8.

38. The start-up process according to claim 14, wherein in the step (3-1), the predetermined value of the input amount of the ammoxidation substrate to the ammoxidation reactor is 1.5-11.4 $Nm^3/h/m^2$, and/or, in the step (3-2), the predetermined value of the input amount of the ammoxidation substrate to the ammoxidation reactor is 9.13-65.8 $Nm^3/h/m^2$, the predetermined value of the input amount of the oxygen-containing gas to the ammoxidation reactor is 82.17-644.9 $Nm^3/h/m^2$.

39. The start-up process according to claim 15, wherein at the beginning of the step (3) or at the beginning of the step (3-1), the content of the molecular oxygen in the reaction tail gas (relative to the total volume of the reaction tail gas) is 7-7.5 vol %, and/or, at the beginning of the step (3-2), the content of the molecular oxygen in the reaction tail gas (relative to the total volume of the reaction tail gas) is 0.5-2 vol %.

40. The start-up process according to claim 17, wherein in the step (1), the temperature of the catalyst bed is ranges from 380° C. to 400° C., inclusive, and/or, wherein in the step (2), the temperature of the catalyst bed is 400-440° C., and/or, in the step (3), the temperature of the catalyst bed is 410-430° C., and/or, in the step (4), the temperature of the catalyst bed is 425-440° C.

41. The start-up process according to claim 18, wherein after the step (2) has proceeded for 5-18 minutes, the step (3) begins, and/or, after the step (3) has proceeded for 8-43 minutes, the step (4) begins, and/or, after the step (4) has proceeded for 6-25 minutes, the start-up process ends, and/or, the time period from the beginning of the step (2) to the end of the start-up process is 20-50 minutes.

42. The start-up process according to claim 19, wherein in the step (2), the predetermined value of the input amount of the ammonia gas to the ammoxidation reactor is 7.5-45.6 $Nm^3/h/m^2$, and the molar ratio of the predetermined value of the input amount of the ammonia gas to the predetermined value of the input amount of the oxygen-containing gas ranges from 1:4-1:7, and/or, in the step (3), the predetermined value of the input amount of the ammoxidation substrate to the ammoxidation reactor is 9.13-65.8 $Nm^3/h/m^2$, and/or, in the step (4), the predetermined value of the input amount of the ammoxidation substrate is 117-143 $Nm^3/h/m^2$, the predetermined value of the input amount of the ammonia gas is 125-185 $Nm^3/h/m^2$, the predetermined value of the input amount of the oxygen-containing gas is 1050-1400 $Nm^3/h/m^2$, the oxygen-containing gas is air.

43. The start-up process according to claim 20, wherein in the step (3-2), increasing the input amount of the oxygen-containing gas and the input amount of ammoxidation substrate to the ammoxidation reactor, wherein the reactor operation linear velocity of the step (3-1) is 0.05-0.15 m/s and the reactor operation linear velocity of the step (3-2) is 0.04-0.17 m/s.

44. The start-up process according to claim 21, wherein the step (3-2) begins after the step (3-1) has proceeded for 3-18 minutes, and/or, wherein the next step is the step (4), wherein the next step begins after the step (3-2) has proceeded for 5-25 minutes, and/or, the time period from the beginning of the step (3-1) to the end of the step (3-2) is 8-43 minutes.

45. The start-up process according to claim 22, wherein in the step (3-1), the temperature of the catalyst bed is 400-415° C., and/or, in the step (3-2), the temperature of the catalyst bed is 425-440° C.

46. The start-up process according to claim 23, wherein in the step (3-1), the input amount of the ammoxidation substrate to the ammoxidation reactor is such an amount that the molar ratio of the ammoxidation substrate to the ammonia gas being input to the ammoxidation reactor ranges from 1:4.5-1:6.5, and/or, in the step (3-2), the input amount of the oxygen-containing gas and the input amount of the ammoxidation substrate to the ammoxidation reactor are increased, so that the molar ratio of the ammoxidation substrate to the ammonia gas being input to the ammoxidation reactor ranges from 1:1.05-1:1.3, and the molar ratio of the ammoxidation substrate to air, as the molecular oxygen, being input to the ammoxidation reactor ranges from 1:9-1:9.8.

47. The start-up process according to claim 24, wherein in the step (3-1), the predetermined value of the input amount of the ammoxidation substrate to the ammoxidation reactor is 1.5-11.4 $Nm^3/h/m^2$, and/or, in the step (3-2), the predetermined value of the input amount of the ammoxidation substrate to the ammoxidation reactor is 9.13-65.8 $Nm^3/h/m^2$, the predetermined value of the input amount of the oxygen-containing gas to the ammoxidation reactor is 82.17-644.9 $Nm^3/h/m^2$.

48. The start-up process according to claim 25, wherein at the beginning of the step (3) or at the beginning of the step (3-1), a content of the molecular oxygen in a reaction tail gas (relative to the total volume of the reaction tail gas) is 7-7.5 vol %, and/or, at the beginning of the step (3-2), the content of the molecular oxygen in the reaction tail gas (relative to the total volume of the reaction tail gas) is 0.5-2 vol %.

49. The start-up process according to claim 26, wherein at the beginning of the step (3) or at the beginning of the step (3-1), the content of the molecular oxygen in the reaction tail gas (relative to the total volume of the reaction tail gas) is 7-7.5 vol %, and/or, at the beginning of the step (3-2), the content of the molecular oxygen in the reaction tail gas (relative to the total volume of the reaction tail gas) is 0.5-2 vol %.

50. The start-up process according to claim 20, wherein at the beginning of the step (3) or at the beginning of the step (3-1), the content of the molecular oxygen in the reaction tail gas (relative to the total volume of the reaction tail gas) is 7.5 vol % or less, and/or, at the beginning of the step (3-2), the content of the molecular oxygen in the reaction tail gas (relative to the total volume of the reaction tail gas) is 2 vol % or less.

51. The start-up process according to claim 27, wherein at the beginning of the step (3) or at the beginning of the step (3-1), a content of the molecular oxygen in a reaction tail gas (relative to the total volume of the reaction tail gas) is 7-7.5 vol %, and/or, at the beginning of the step (3-2), the content of the molecular oxygen in the reaction tail gas (relative to the total volume of the reaction tail gas) is 0.5-2 vol %.

* * * * *